United States Patent
Zebala

(12) 
(10) Patent No.: US 11,404,168 B1
(45) Date of Patent: Aug. 2, 2022

(54) TARGETED VENUE BASED MESSAGE AND COMMUNICATION DISTRIBUTION BASED ON PROXIMITY DATA

(71) Applicant: Vaxley, Inc., Auburn, WA (US)

(72) Inventor: John Anthony Zebala, Auburn, WA (US)

(73) Assignee: VAXLEY, INC., Auburn, WA (US)

( * ) Notice: Subject to any disclaimer, the term of this patent is extended or adjusted under 35 U.S.C. 154(b) by 0 days.

(21) Appl. No.: 17/461,751

(22) Filed: Aug. 30, 2021

(51) Int. Cl.
| | |
|---|---|
| *G16H 50/80* | (2018.01) |
| *H04W 4/021* | (2018.01) |
| *G16H 10/60* | (2018.01) |
| *G07C 9/38* | (2020.01) |
| *G16H 50/70* | (2018.01) |
| *G06F 21/62* | (2013.01) |
| *G16H 10/40* | (2018.01) |
| *G06V 30/10* | (2022.01) |
| *G06V 30/40* | (2022.01) |

(52) U.S. Cl.
CPC ......... *G16H 50/80* (2018.01); *G06F 21/6245* (2013.01); *G07C 9/38* (2020.01); *G16H 10/40* (2018.01); *G16H 10/60* (2018.01); *G16H 50/70* (2018.01); *H04W 4/021* (2013.01); *G06V 30/10* (2022.01); *G06V 30/40* (2022.01)

(58) Field of Classification Search
CPC ........ G16H 50/80; G16H 10/40; G16H 10/60; G16H 50/70; G06F 21/6245
See application file for complete search history.

(56) References Cited

U.S. PATENT DOCUMENTS

| | | | |
|---|---|---|---|
| 10,380,814 B1 * | 8/2019 | Mathiesen | G07C 9/253 |
| 11,151,820 B1 * | 10/2021 | Klein | G16H 10/40 |
| 2006/0279431 A1 * | 12/2006 | Bakarania | A61B 5/14532 340/870.02 |
| 2009/0070361 A1 * | 3/2009 | Haber | G06F 21/6254 |
| 2017/0134905 A1 * | 5/2017 | Venkatesan | H04W 4/021 |

OTHER PUBLICATIONS

Eilish O'Reagan, "Virus growth rate halves but fears over testing delay", 2020, pp. 1-3 (Year: 2020).*
PR Newswire, "US Will Reach Herd Immunity Threshold by Mid-Summer According to Oliver Wyman", Mar. 2021, pp. 1-2 (Year: 2021).*

* cited by examiner

*Primary Examiner* — Jason B Dunham
*Assistant Examiner* — Steven G. S. Sanghera
(74) *Attorney, Agent, or Firm* — Shah IP Law, PLLC

(57) ABSTRACT

Disclosed herein are systems and methods for immunity data creation and immunity monitoring (e.g., management, maintenance, etc.). A user may upload immunity and redaction data. A community of other users may verify the uploaded data. A venue may comprise a target immunity level and an actual immunity level. Combining the verified uploaded data with the actual immunity level may yield a new actual immunity level. The user may be allowed to enter the venue if the new actual immunity level is at or above the target immunity level.

22 Claims, 17 Drawing Sheets

FIG. 3C

TARGETED VENUE BASED MESSAGE AND COMMUNICATION DISTRIBUTION BASED ON PROXIMITY DATA

CROSS-REFERENCE TO RELATED APPLICATIONS

None.

BACKGROUND

Field of Art

The present invention is in the field of communication and messaging. More particularly, the present invention is in the field of targeted delivery of messages based on proximity of a user to one or more venues and the identified status of the user.

Discussion of the State of the Art

Entertainment and event venues such as theme parks, cruise ships, universities, arenas, concert venues, restaurants, ski resorts, relaxation resorts, ice rinks, spas, skate parks, and stadiums typically have large numbers of visitors/guests and typically do not have the ability to communicate with their visitors/guests at a granular level and/or differentiate the visitors/guests based on one or more status identifier associated with the visitors/guests. Typically, an entertainment venue wanting to send a message to its guests would need to send the message to all visitors at once, such as, by sending a message to all registered ticket holders, students, staff, or the like. Such a message may not be relevant to all guests of the entertainment venue, but would be sent to all guests regardless.

Entertainment venues typically do not have access to information about each of their guests, such as the guest's identity as well as the guest's location (or proximity to points of interest) at any particular time of day. More generally, entertainment venues typically do not even know how many guests are within the venue at a given time, and therefore, are unable to send targeted messages based on a status or an identifier associated with the user.

This issue has been exacerbated by the spread of highly contagious viruses such as SARS Covid-19, which has spread globally despite many different preventive measures that have been put in place to reduce transmission. Some countries aimed for suppression by extreme quarantine measures (lockdown) and others aimed for mitigation by slowing the spread using certain preventive measures (e.g., masking, social distancing) in combination with protection of the vulnerable. More recently, several effective vaccines have been approved and been made available in widespread distribution. It was hoped that with the availability of vaccines, preventive measures could be eased and eventually abandoned such that society could return to pre-pandemic life involving unrestricted social gatherings in restaurants, bars, theaters, stadiums, gyms, retail stores, schools and numerous other settings where human mixing and the potential for viral transmission is dominant. However, the hope of returning to pre-pandemic life has been met by several obstacles, such as a reluctance to vaccinate. What is needed are systems and methods that facilitate a return to pre-pandemic life within the constraints of reality.

More specifically, there is a need for systems and methods that facilitate communication between venues and visitors/guests based on a granular understanding of one or more status or identifiers associated with each visitor/guest.

SUMMARY

Disclosed herein are computer implemented systems and methods for enabling communication between a venue and maintaining an immunity level at a venue that equals or exceeds a target immunity level based on immunity data associated with a user and the target immunity level associated with the venue. Immunity may result from vaccination or disease immunity from previous resolved infection. The immunity level at a venue is the number of people at the venue with immunity divided by the total number of people at the venue. An example computer implemented method may comprise receiving location data from a computing device associated with the user. The example computer implemented method may comprise computing a geofence associated with the received location data. The example computer implemented method may comprise identifying venue data associated with at least one venue associated with the computed geofence. Each venue may be associated with a target immunity level. The example computer implemented method may comprise obtaining immunity data associated with the user. The immunity data may be obtained from a database. The database may be at least partially populated from data provided by the user. The example computer implemented method may comprise computing a current immunity level associated with each venue. The current immunity level may be computed based on immunity data associated with each venue occupant who has provided immunity data in association with entering, and optionally also exiting, the corresponding venue. The example computer implemented method may comprise determining whether the user is enabled to access each venue based on a permissions computation comprising a projected immunity level for each venue. The projected immunity level may be calculated based on data associated with the computed current immunity level and immunity data of the user, and comparing the projected immunity level if the user were to access each venue with the target immunity level associated with the venue. The example computer implemented method may comprise providing, to the computing device associated with the user, venue data associated with each venue that the user is enabled to access based on the permissions computation, the provided venue data, target immunity level, and current immunity level capable of being displayed on the computing device associated with the user. The example computer implemented method may comprise granting or denying the user access to each venue based on the permissions computation. The example computer implemented method may comprise thereby maintaining an immunity level at each venue that equals or exceeds the target immunity level associated with each venue.

Disclosed herein are computer implemented methods for immunity data creation. An example computer implemented method may comprise receiving user information comprising vaccination information. The example computer implemented method may comprise receiving redacted information. The example computer implemented method may comprise verifying redacted user information. The example computer implemented method may comprise storing verification data in association with the user information.

BRIEF DESCRIPTION OF THE DRAWING FIGURES

The accompanying drawings illustrate several embodiments and, together with the description, serve to explain the principles of the invention according to the embodiments. It will be appreciated by one skilled in the art that the particular arrangements illustrated in the drawings are merely exemplary and are not to be considered as limiting of the scope of the invention or the claims herein in any way.

FIG. 3C illustrates a user interface in accordance with an exemplary embodiment of the invention.

DETAILED DESCRIPTION OF EMBODIMENTS

Figure 1A:
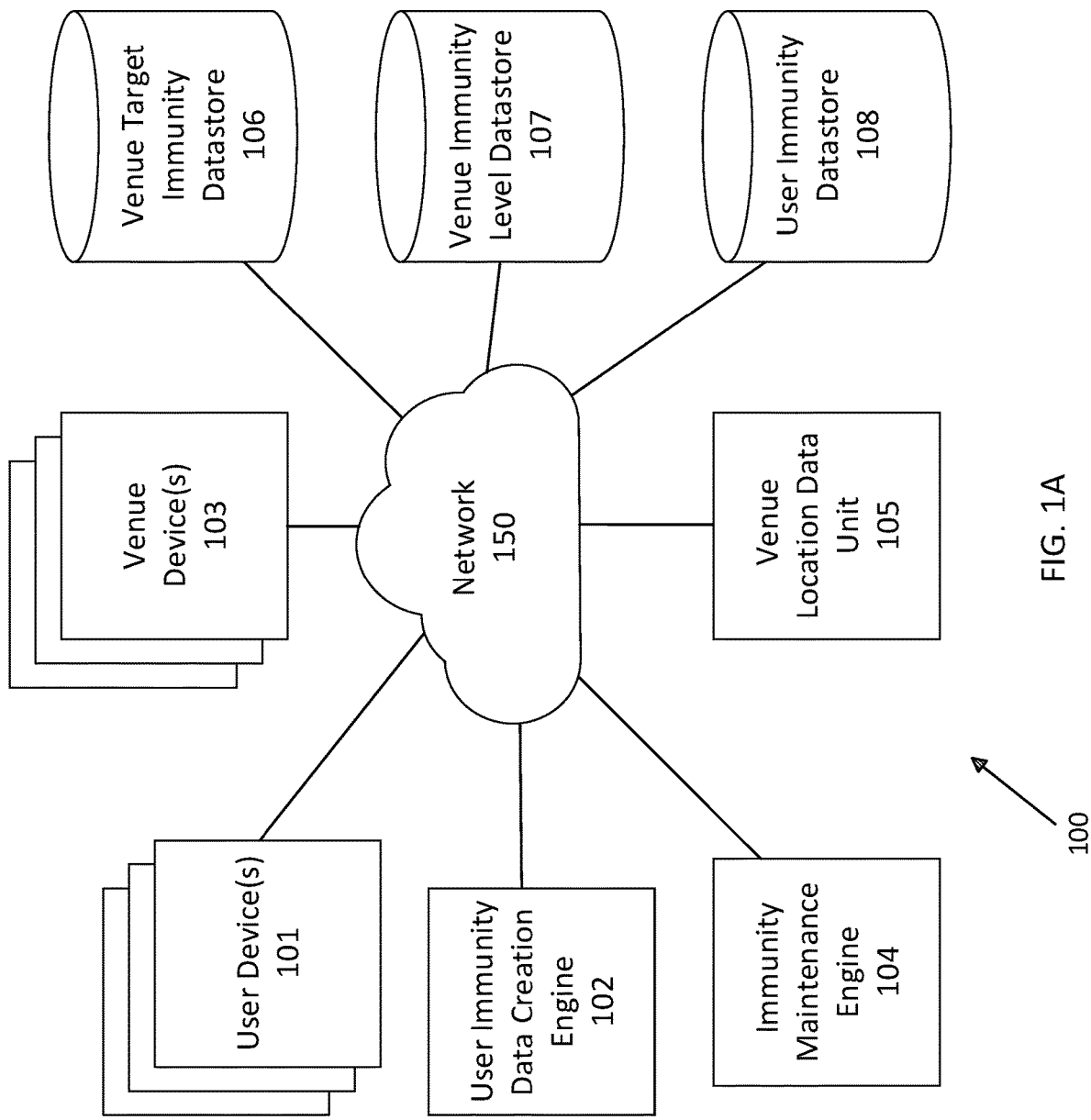
FIG. 1A illustrates an environment for immunity data creation and immunity monitoring in accordance with an exemplary embodiment of the invention.

The inventive system and method (hereinafter sometimes referred to more simply as "system" or "method") described herein enable immunity data creation and immunity monitoring (e.g., management, maintenance, etc.). Specifically, the systems and methods disclosed herein allow for monitoring and/or enforcement of the near real-time immunity levels across each of tens-of-thousands to millions of person-to-person mixing points to inform health policy decisions of governmental authorities that will cause Covid-19 transmission to decline. The systems and methods disclosed herein allow for enabling people to gather in venues in the absence of preventive measures without also increasing the transmission of Covid-19 in the population or using the binary model of venue access (i.e., vaccinated person allowed entry, and unvaccinated persons denied entry; i.e., "vaccine passports"). The systems and methods disclosed herein allow for decreasing the transmission of Covid-19 in the population without preventive measures when the proportion of the population vaccinated is below the level required for herd immunity. The systems and methods disclosed herein allow for enabling a person to create a digital immunity token for vaccine or disease immunity using only their paper vaccination card or antibody/prior infection test result, respectively, and without necessarily accessing their electronic medical record, without using proprietary electronic medical records software, and without accessing government-specific vaccination databases. In at least some embodiments, "medical record" may be a printed record displayed on paper or electronically (e.g., by a computer or smartphone screen) that indicates whether a person has vaccine immunity or disease immunity. Some examples of a medical record comprise a vaccination card, antibody test result, prior infection test result, immunity record, etc. The digital immunity token is optionally further validated.

One or more different embodiments may be described in the present application. Further, for one or more of the embodiments described herein, numerous alternative arrangements may be described; it should be appreciated that these are presented for illustrative purposes only and are not limiting of the embodiments contained herein or the claims presented herein in any way. One or more of the arrangements may be widely applicable to numerous embodiments, as may be readily apparent from the disclosure. In general, arrangements are described in sufficient detail to enable those skilled in the art to practice one or more of the embodiments, and it should be appreciated that other arrangements may be utilized and that structural, logical, software, electrical and other changes may be made without departing from the scope of the embodiments. Particular features of one or more of the embodiments described herein may be described with reference to one or more particular embodiments or figures that form a part of the present disclosure, and in which are shown, by way of illustration, specific arrangements of one or more of the aspects. It should be appreciated, however, that such features are not limited to usage in the one or more particular embodiments or figures with reference to which they are described. The present disclosure is neither a literal description of all arrangements of one or more of the embodiments nor a listing of features of one or more of the embodiments that must be present in all arrangements.

Headings of sections provided in this patent application and the title of this patent application are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible embodiments and in order to more fully illustrate one or more embodiments. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the embodiments, and does not imply that the illustrated process is preferred. Also, steps are generally described once per aspect, but this does not mean they must occur once, or that they may only occur once each time a process, method, or algorithm is carried out or executed. Some steps may be omitted in some embodiments or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various embodiments in which, for example, functions may be executed out of order from that shown or discussed, including substantially concurrently or in reverse order, depending on the functionality involved, as would be understood by those having ordinary skill in the art.

FIG. 1A illustrates an environment 100 for immunity data creation and immunity monitoring (e.g., management, maintenance, etc.) in accordance with an exemplary embodiment of the invention. The environment 100 comprises one or more user device(s) 101, a user immunity data creation engine 102, one or more venue device(s) 103, a immunity maintenance engine 104, a venue location data unit 105, a venue target immunity datastore 106, a venue immunity level datastore 107, a user immunity datastore 108, and a network 150. The various computing devices described herein are exemplary and for illustration purposes only. The system may be reorganized or consolidated, as understood by a person of ordinary skill in the art, to perform the same tasks on one or more other servers or computing devices without departing from the scope of the invention.

The one or more user device(s) 101 may be in communication with one or more of the user immunity data creation engine 102, one or more other user device(s) 101, one or more venue device(s) 103, the immunity maintenance engine 104, the venue location data unit 105, the venue target immunity datastore 106, the venue immunity level datastore 107, and/or the user immunity datastore 108 via the network 150. The one or more user device(s) 101 (herein referred to as user input device, computing device, or client device) may include, generally, a computer or computing device including functionality for communicating (e.g., remotely) over the network 150. One or more user device(s) 101 may be a server, a desktop computer, a laptop computer, personal digital assistant (PDA), an in- or out-of-car navigation system, a smart phone or other cellular or mobile phone, or mobile gaming device, among other suitable computing devices. One or more user device(s) 101 may execute one or more client applications, such as a web browser (e.g., Microsoft Windows Internet Explorer, Mozilla Firefox, Apple Safari, Google Chrome, and Opera, etc.), or a dedicated application for immunity data creation and immunity monitoring.

In particular embodiments, each one or more user device(s) 101 may be an electronic device including hardware, software, or embedded logic components or a combination of two or more such components and capable of carrying out the appropriate functions implemented or supported by the one or more user device(s) 101. For example and without limitation, one or more user device(s) 101 may be a desktop computer system, a notebook computer system, a netbook computer system, a handheld electronic device, or a mobile telephone. The present disclosure contemplates any user device as the one or more user device(s) 101. The one or more user device(s) 101 may enable a network user at the one or more user device(s) 101 to access network 150. The one or more user device(s) 101 may enable its user to communicate with other users at other one or more user device(s) 101.

The one or more user device(s) 101 may have a web browser, such as MICROSOFT INTERNET EXPLORER, GOOGLE CHROME or MOZILLA FIREFOX, and may have one or more add-ons, plug-ins, or other extensions, such as TOOLBAR or YAHOO TOOLBAR. The one or more user device(s) 101 may enable a user to enter a Uniform Resource Locator (URL) or other address directing the web browser to a server, and the web browser may generate a Hyper Text Transfer Protocol (HTTP) request and communicate the HTTP request to server. The server may accept the HTTP request and communicate to the one or more user device(s) 101 one or more Hyper Text Markup Language (HTML) files responsive to the HTTP request. The one or more user device(s) 101 may render a web page based on the HTML files from the server for presentation to the user. The present disclosure contemplates any suitable web page files. As an example and not by way of limitation, web pages may render from HTML files, Extensible Hyper Text Markup Language (XHTML) files, or Extensible Markup Language (XML) files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a web page encompasses one or more corresponding web page files (which a browser may use to render the web page) and vice versa, where appropriate.

The one or more user device(s) 101 may also include an application (e.g., an "app") that is loaded onto the one or more user device(s) 101. The application may be written as a native app (e.g., using Swift, Objective C, Java or Kotlin), a hybrid app (e.g., using React Native, Appcelerator, Flutter, Dart, or Cordova/PhoneGap) or as a progressive web application (PWA). The application may obtain data from the network 150 and displays it to the user within the application interface.

This disclosure contemplates any suitable number of one or more user device(s) 101, including computing systems taking any suitable physical form. As example and not by way of limitation, computing systems may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, or a combination of two or more of these. Where appropriate, the computing system may include one or more computer systems; be unitary or distributed; span multiple locations; span multiple machines; or reside in a cloud, which may include one or more cloud components in one or more networks. Where appropriate, one or more computing systems may perform without substantial spatial or temporal limitation one or more steps of one or more methods described or illustrated herein. As an example, and not by way of limitation, one or more computing systems may perform in real time or in batch mode one or more steps of one or more methods described or illustrated herein. One or more computing system may perform at different times or at different locations one or more steps of one or more methods described or illustrated herein, where appropriate.

In embodiments, the one or more user device(s) 101 may comprise mobile devices (e.g., phones, tablets, etc.) such that the one or more user device(s) 101 may be used for presentation of immunity data at venues. Immunity data may comprise direct immunity data (e.g., vaccination card image, antibody or prior infection test result image, immunity record, etc.) and/or immunity reference data (e.g., immunity token, immunity identifier, etc.). The immunity reference data may comprise a Quick Response (QR) code. Example immunity data for presentation at venues is shown in reference to FIG. 1B. A single user device 101 may comprise a plurality of immunity data sets (e.g., immunity tokens, immunity identifiers, vaccination card images, antibody/prior infection test result images, etc.) such as a parent having their personal immunity token as well as immunity tokens for their children or other family/group members.

The one or more user device(s) 101 may comprise the one or more venue device(s) 103. The one or more venue device(s) 103 may comprise any device configured to receive immunity data. Receiving immunity data may comprise scanning (e.g., reading, interpreting, etc.) a QR code associated with user immunity data. The one or more venue device(s) 103 may comprise any device configured to query the user immunity datastore 108 via the network 150 and display the query results. The query results may comprise data derived from paper and/or digital immunity records (e.g., vaccination information, test results, etc.). Example user immunity datastore 108 query results shown on a venue device 103 after an interaction with a user device 101 is shown in reference to FIG. 1D. The one or more venue device(s) 103 may comprise any device configured to view and/or update a venue's associated target immunity level in the venue target immunity datastore 106 and/or the venue's associated current immunity level in the venue immunity level datastore 107. An example interface facilitating viewing and/or modification of data associated with a venue in the venue target immunity datastore 106 and/or the venue immunity level datastore 107 is shown in reference to FIG. 1E.

The user immunity data creation engine 102 may comprise software and/or hardware for immunity data creation. The user immunity data creation engine 102 may be configured to generate immunity data, such as creating an immunity record, an immunization card image, antibody or prior infection test result image, an immunity token, an immunity identifier, etc. The user immunity data creation engine 102 will be described in more detail in reference to FIG. 3A. Generally, the user immunity data creation engine 102 may receive user profile information (such as name, date of birth, a photograph of the user, etc.) and immunity information (such as a vaccine brand (e.g., manufacturer, creator, sponsor, etc.), a dosage, a dose lot number, a vaccination date, a location, a physician name, an expiration date, a country, a card type, antibody test date, antibody test result, positive infection test result, etc.). Received information may be manually entered. An example interface for manually entering information is shown in reference to FIG. 3B. Received information may be a received digital image, such as an image of an identification card, test results or a vaccination card. An example interface for receiving a digital image is shown in reference to FIG. 3B. The user immunity data creation engine 102 may perform optical character recognition (OCR) on a received digital image and extract relevant immunity data from the digital image. Although shown as a separate server connected to the network 150 in FIG. 1, in other embodiments, the user immunity data creation engine 102 may reside elsewhere in the environment 100. For example, the user immunity data creation engine 102 may reside, at least partially, in software in an application executing on at least one of the one or more user device(s) 101.

The user immunity data creation engine 102 may be in communication with the user immunity datastore 108 via the network 150. The user immunity data creation engine 102 may create direct immunity data (e.g., vaccination card image, antibody or prior infection test result image, immunity record, etc.) and cause the direct immunity data to be stored in the user immunity datastore 108. The user immunity data creation engine 102 may create immunity reference data (e.g., immunity token, immunity identifier, etc.), which, when accessed, may cause corresponding direct immunity data to be retrieved from the user immunity datastore 108. The user immunity datastore 108 may comprise a centralized database located in one or more computing devices. The user immunity datastore 108 may comprise a distributed ledger or blockchain.

The venue location data unit 105 may comprise software and/or hardware for providing venue location data in proximity to a user device 101 or within a search area specified by a user. Example interfaces for the venue location data unit 105 are shown in reference to FIG. 2B and FIG. 2C. Although shown as a separate server connected to the network 150 in FIG. 1, in other embodiments, the venue location data unit 105 may reside elsewhere in the environment 100. For example, the venue location data unit 105 may reside, at least partially, in software in an application executing on at least one of the one or more user device(s) 101.

The one or more venue device(s) 103 may be in communication with the venue target immunity datastore 106 via the network 150. Each venue may use a corresponding at least one of the one or more venue device(s) 103 to specify a preferred target immunity level and/or specify a level set by governmental rules and/or regulations and store the associated preferred target immunity level in the venue target immunity datastore 106. The preferred target immunity levels stored in the venue target immunity datastore 106 may be accessible on the one or more user device(s) 101 via the network 150. An example interface facilitating viewing and/or modification of data associated with a venue in the venue target immunity datastore 106 is shown in reference to FIG. 1E. The venue target immunity datastore 106 may comprise a centralized database located in one or more computing devices. The venue target immunity datastore 106 may comprise a distributed ledger or blockchain.

The one or more venue device(s) 103 may be in communication with the venue immunity level datastore 107 via the network 150. Each venue may use a corresponding at least one of the one or more venue device(s) 103 to specify an entry to or exit of a particular person with a particular immunity status (e.g., vaccine immunity, disease immunity, no immunity) into or out of the venue in the venue immunity level datastore 107. The venue immunity level datastore 107 may store historic data associated with the achieved immunity levels associated with each venue over time. Immunity level changes may be recorded as a function of time and the immunity status of the users who enter and/or exit the venue in the venue immunity level datastore 107. Immunity data may be recorded in the venue immunity level datastore 107 such that for any given time and/or inquiry, the immunity level for the present, past hour, day, week, month, etc. may be computed and presented to one or more user device(s) 101 and/or one or more venue device(s) 103 via the network 150. An example interface facilitating viewing and/or modification of data associated with a venue in the venue immunity level datastore 107 is shown in reference to FIG. 1D. The venue immunity level datastore 107 may comprise a centralized database located in one or more computing devices. The venue immunity level datastore 107 may comprise a distributed ledger or blockchain.

The immunity maintenance engine 104 may comprise software and/or hardware for immunity data monitoring (e.g., management, maintenance, etc.). The immunity maintenance engine 104 may be configured to receive location information associated with a user and/or venue, venue immunity level data, venue target immunity level data and user immunity data, and perform calculations to determine projected venue immunity levels if a user were to visit a given venue, and determine whether the user visiting the given venue would put the venue below an associated target immunity level. The immunity maintenance engine 104 will be described in more detail in reference to FIG. 2A. Although shown as a separate server connected to the network 150 in FIG. 1, in other embodiments, the immunity maintenance engine 104 may reside elsewhere in the environment 100. For example, the immunity maintenance engine 104 may reside, at least partially, in software in an application executing on at least one of the one or more venue device(s) 103.

The network 150 may facilitate communication between the one or more user device(s) 101, the user immunity data creation engine 102, the one or more venue device(s) 103, the immunity maintenance engine 104, the venue location data unit 105, the venue target immunity datastore 106, the venue immunity level datastore 107, and the user immunity datastore 108.

The network 150 generally represents a network or collection of networks (such as the Internet or a corporate intranet, or a combination of both) over which the various components illustrated in FIG. 1 are connected and which connects the various systems and computing devices described or referenced herein (including other components that may be necessary to execute the system described herein, as would be readily understood to a person of ordinary skill in the art). In particular embodiments, network 150 is an intranet, an extranet, a virtual private network (VPN), a local area network (LAN), a wireless LAN (WLAN), a wide area network (WAN), a metropolitan area network (MAN), a portion of the Internet, or another network 150 or a combination of two or more such networks 150. One or more links connect the systems and databases described herein to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable network 150, and any suitable link for connecting the various systems and databases described herein.

One or more links couple one or more systems, engines or devices to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable links coupling one or more systems, engines or devices to the network 150.

In particular embodiments, each system or engine may be a unitary server or may be a distributed server spanning multiple computers or multiple datacenters. Systems, engines, or modules may be of various types, such as, for example and without limitation, web server, news server, mail server, message server, advertising server, file server, application server, exchange server, database server, or proxy server. In particular embodiments, each system, engine or module may include hardware, software, or embedded logic components or a combination of two or more such components for carrying out the appropriate functionalities implemented or supported by their respective servers. For example, a web server is generally capable of hosting websites containing web pages or particular elements of web pages. More specifically, a web server may host HTML files or other file types, or may dynamically create or constitute files upon a request, and communicate them to one or more computing device(s) or other devices in response to HTTP or other requests from one or more computing device(s) or other devices. A mail server is generally capable of providing electronic mail services to various one or more computing device(s) or other devices. A database server is generally capable of providing an interface for managing data stored in one or more data stores.

In particular embodiments, one or more data storages may be communicatively linked to one or more servers via one or more links. In particular embodiments, data storages may be used to store various types of information. In particular embodiments, the information stored in data storages may be organized according to specific data structures. In particular embodiments, each data storage may be a relational database. Particular embodiments may provide interfaces that enable servers or clients to manage, e.g., retrieve, modify, add, or delete, the information stored in data storage.

The system may also contain other subsystems and databases, which are not illustrated in FIG. 1, but would be readily apparent to a person of ordinary skill in the art. For example, the system may include databases for storing data, storing features, storing outcomes (training sets), and storing models. Other databases and systems may be added or subtracted, as would be readily understood by a person of ordinary skill in the art, without departing from the scope of the invention.

Figure 1B:
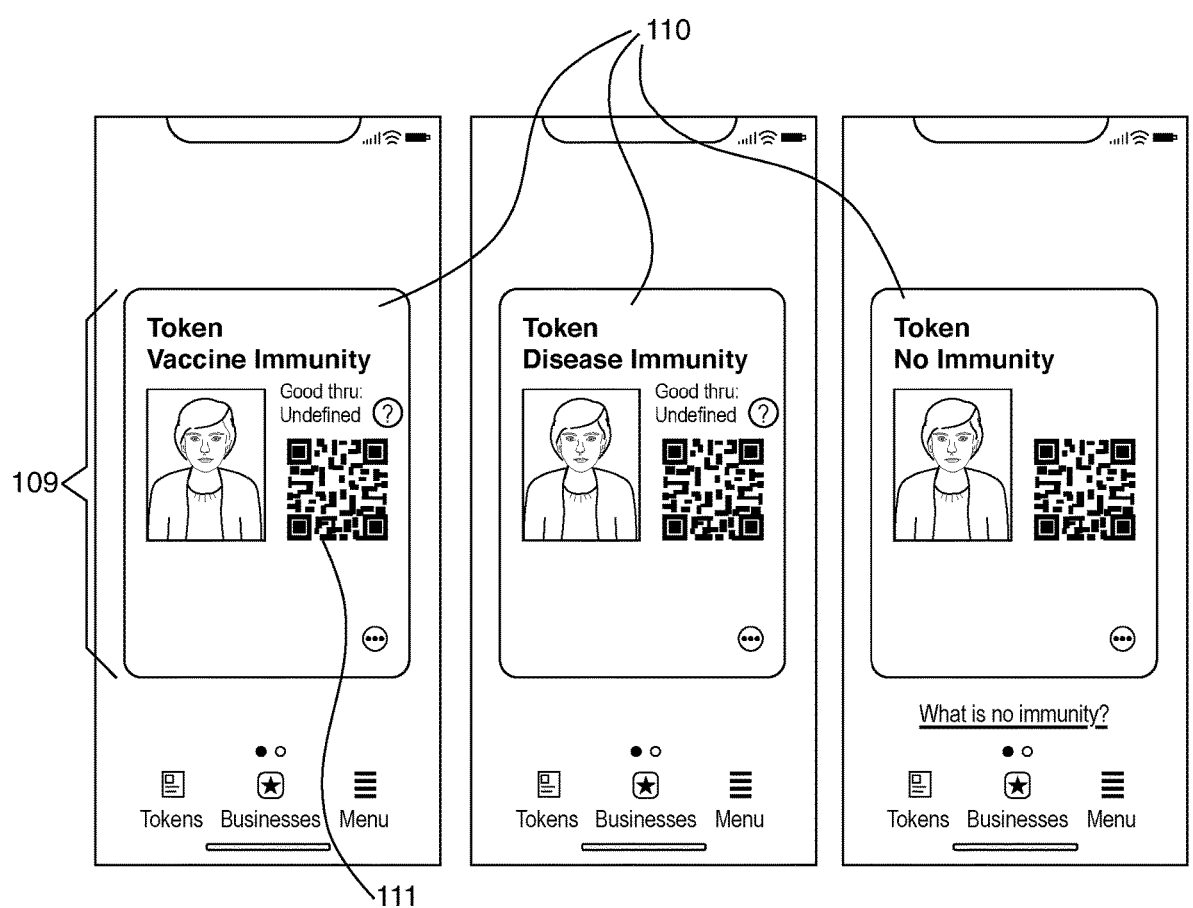
FIG. 1B illustrates user interfaces in accordance with an exemplary embodiment of the invention.

FIG. 1B illustrates a user interface in accordance with an exemplary embodiment of the invention. The user interface shows what may be shown on one of the one or more user device(s) 101. The interface may comprise a set of fields 109, a representation (e.g., icon, emoticon, emoji, picture, phrase, word, letter, character, etc.) indicative of a immunity status 110, and immunity reference data (e.g., immunity token, immunity identifier, etc.) 111. The set of fields 109 may also comprise user profile data, such as a name, date of birth, validation status, etc. which may be displayed at 109. The representation indicative of immunity status 110 may comprise text or a positive indication, such as a checkmark, a green color, a thumbs up emoji, etc. The representation indicative of immunity status 110 may comprise text or a negative indication, such as a X, a red color, a thumbs down emoji, etc. An immunity status 110 with a positive indication may indicate that a corresponding user has immunity for a given disease. A verification status 110 with a negative indication may indicate that a corresponding user does not have immunity for a given disease. The immunity reference data 111 may comprise a QR code. On scanning the immunity reference data 111, corresponding immunity direct data, such as redacted immunity records, may be accessed. The interface may comprise a set of fields 109, a representation indicative of immunity status 110, and immunity reference data 111 for multiple users, such as for spouses, children, parents, coworkers, etc.

Figure 1C:
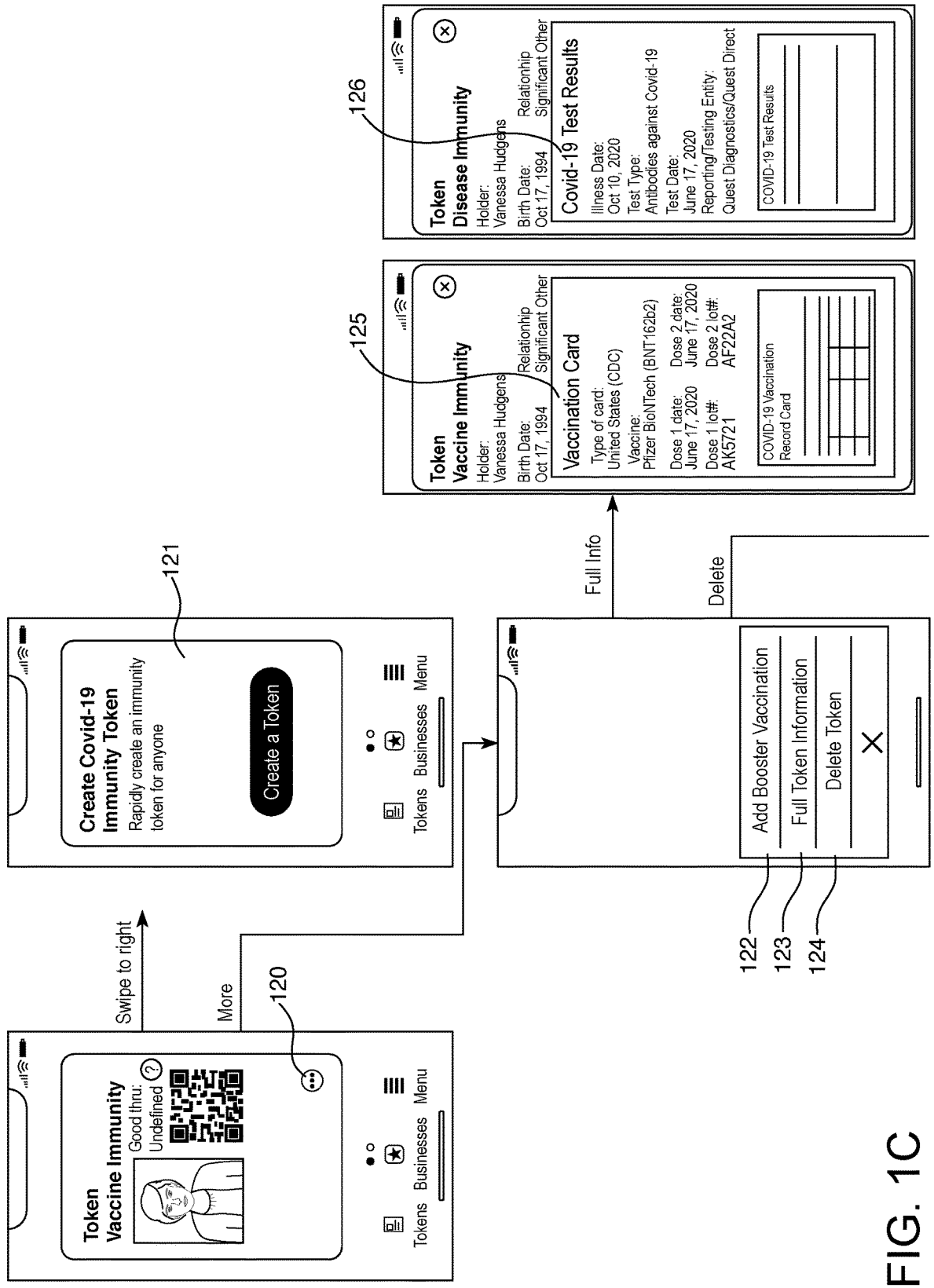
FIG. 1C illustrates a user interface in accordance with an exemplary embodiment of the invention.

FIG. 1C illustrates a user interface in accordance with an exemplary embodiment of the invention. The user interface shows what may be shown on one of the one or more user device(s) 101. The depicted interface shows an exemplary interface through which a user can perform multiple functions such as creating a new token 121, viewing full token information 123 such as vaccination card information 125 and test result information 126, editing token information such as adding additional vaccinations or test results 122 (e.g. booster vaccination, a different vaccination, test result, etc.), and deleting a token 124. These functions may be activated by interacting with the user interface via swiping (e.g. left/right, up/down) or via a button or icon 120 to cause the display of the appropriate user interface elements associated with each function.

Figure 1D:
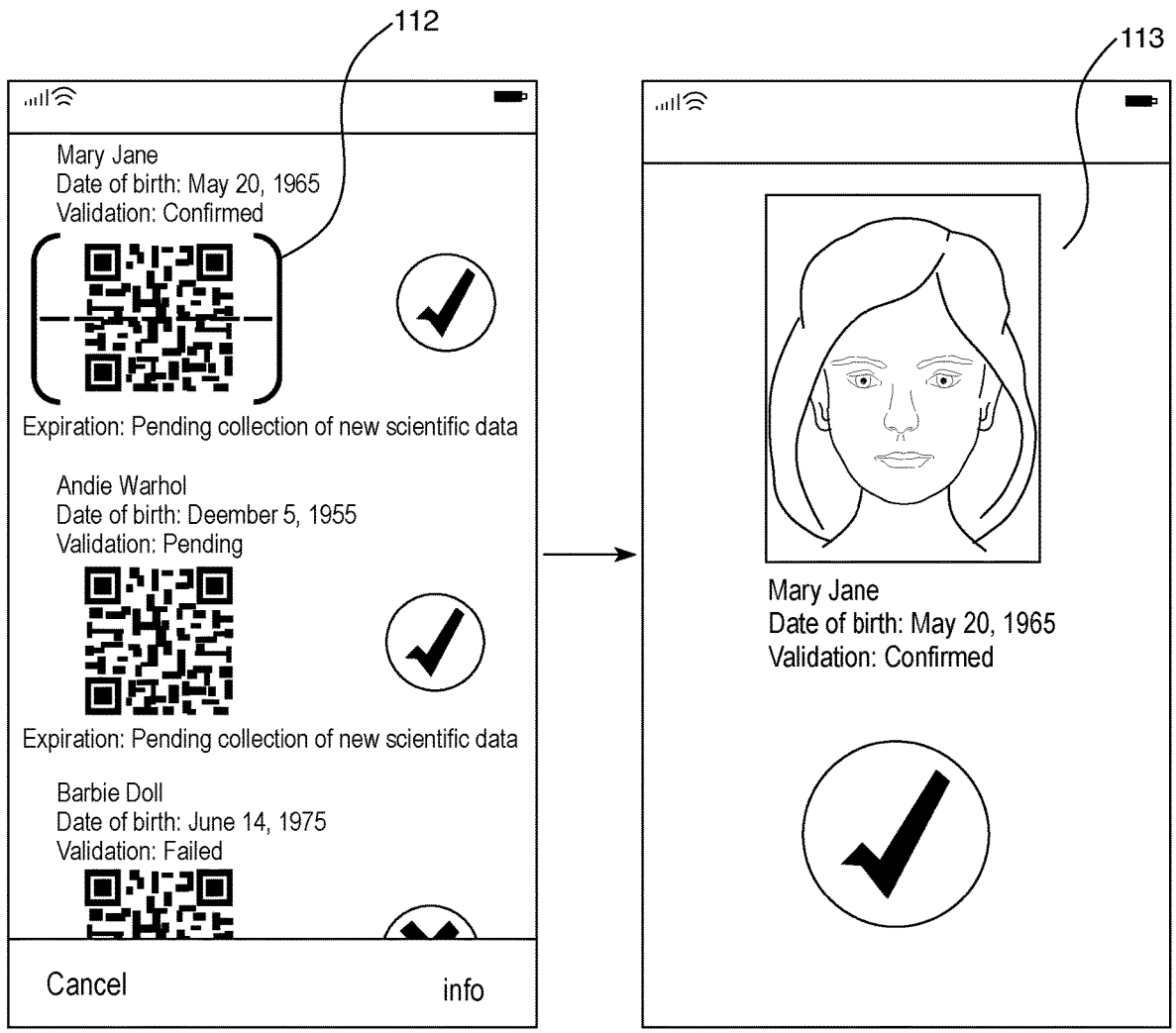
FIG. 1D illustrates a user interface in accordance with an exemplary embodiment of the invention.

FIG. 1D illustrates user interfaces in accordance with an exemplary embodiment of the invention. The user interface shows what may be shown on one of the one or more venue device(s) 103. FIG. 1D (left) depicts what may be displayed on venue device(s) 103 during the act of scanning user immunity data such as a user provided immunity token comprising user immunity reference data, similar to that depicted in FIG. 1B. In this embodiment, user interface may comprise a guide 112 indicating to a user of venue device(s) 103, the area being scanned, which in the case of FIG. 1B is depicted as scanning a first of a plurality of user immunity reference data in view of a camera associated with a venue device 103. FIG. 1B (right) depicts an interface on a venue device showing what happens when immunity reference data is scanned. After scanning, the displayed interface on the venue device may comprise a profile picture, a set of fields, and a verification status 113. The set of fields may comprise a user name, a date of birth, an indication of a verification status, etc.

Figure 1E:
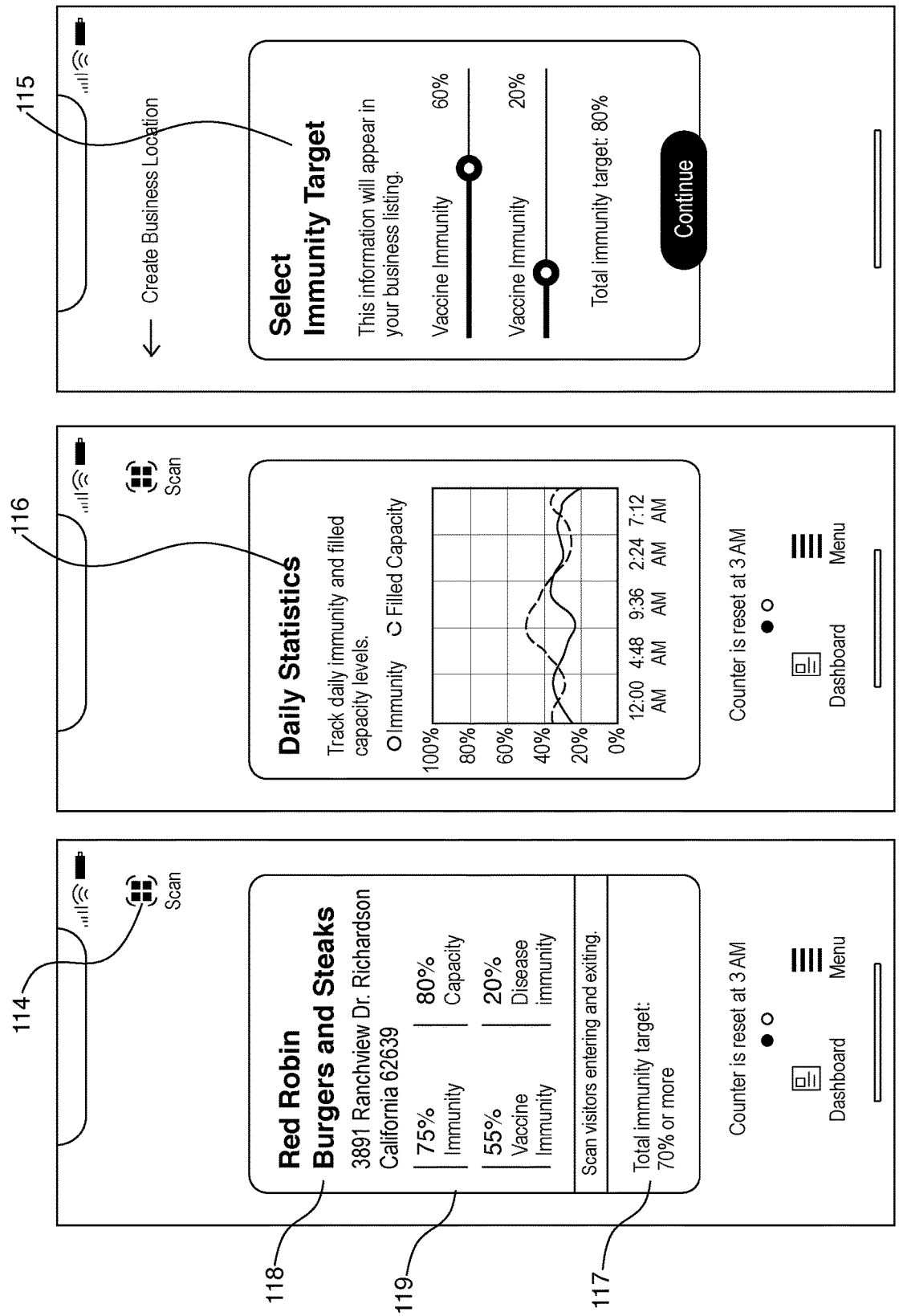
FIG. 1E illustrates a user interface in accordance with an exemplary embodiment of the invention.

FIG. 1E illustrates a user interface in accordance with an exemplary embodiment of the invention. The user interface shows an exemplary business dashboard showing one example of how aggregated data for a venue may be shown on the one or more venue device(s) 103 and various interfaces through which users associated with a venue can view venue statistics, modify venue immunity targets, and initiate scanning of user/patron immunity reference data. The user interface may comprise venue information (such as name, address, etc.) 118, an icon (e.g., button, link, clickable element, etc.) to activate an interface for receiving immunity reference data 114, an interface for changing a target immunity level for a venue 115, a display of the target immunity level 117, a listing of actual historical immunity levels 116, a breakdown of immunity level statistics 119 such as the portion of immunity associated with vaccine immunity, the portion of immunity associated with disease immunity and a total immunity, etc. The listing of actual historical immunity levels 116 may comprise indications of actual levels, associated times and/or dates, an indication of whether the actual level was at or above the target immunity level, and an indication of percentage of filled capacity over time, etc. While depicted here in graphical format, immunity and/or capacity levels 116 may also be displayed in numerical format, such as text based metrics indicating immunity and/or capacity for time periods comprising hourly, daily, weekly, etc.

A user may use a user device 101 to input vaccine information. The user may take a picture of a vaccine card and redact sensitive information on a digital representation of the card. The user device 101 may transmit inputted vaccine information and redacted information to the user immunity data creation engine 102 via the network 150. The user immunity data creation engine 102 may extract data from the vaccine information and suppress information indicated to be concealed by redacting information. The user immunity data creation engine 102 may transmit extracted data to the user immunity datastore 108 via the network 150. The user immunity data creation engine 102 may transmit a QR code and/or at least a portion of the extracted data to the user device 101, wherein the QR code facilitates access to the extracted data stored in the user immunity data creation engine 102.

The user may use the user device 101 to access the venue location data unit 105 via the network 150. The venue location data unit 105 may cause participating venues within a certain distance (e.g., parameter, range, etc.) to be displayed on the user device 101. The user may select a venue of the displayed participating venues and travel to the selected venue. The user may arrive at the venue and cause the QR code to be presented on a screen on the user device 101, similar to the interface shown on FIG. 1B. An employee at the venue may use a venue device 103 to scan the QR code and transmit scanned data to the immunity maintenance engine 104 via the network 150. On scanning, the venue device 103 may receive immunity data from the user immunity datastore 108 and display user immunity data on the venue device, similar to the interfaces shown on FIG. 1D. Prior to and after completion of engagement with the QR code, the venue device 103 may display historical immunity data for the venue, similar to the interface shown on FIG. 1E.

The immunity maintenance engine 104 may retrieve an actual immunity level associated with the venue from the venue immunity level datastore 107. The immunity maintenance engine 104 may compute a projected immunity level based on the retrieved actual immunity level and the scanned data. The immunity maintenance engine 104 may retrieve a target immunity level associated with the venue from the venue target immunity datastore 106. The immunity maintenance engine 104 may compare the computed projected immunity level with the retrieved target immunity level. If the computed projected immunity level is at or above the retrieved target immunity level, then the user may be admitted into the venue and data associated with the venue in the venue immunity level datastore 107 may be updated with the computed projected immunity level. If the computed projected immunity level is below the retrieved target immunity level, then the user may be denied entry into the venue.

Figure 2A:
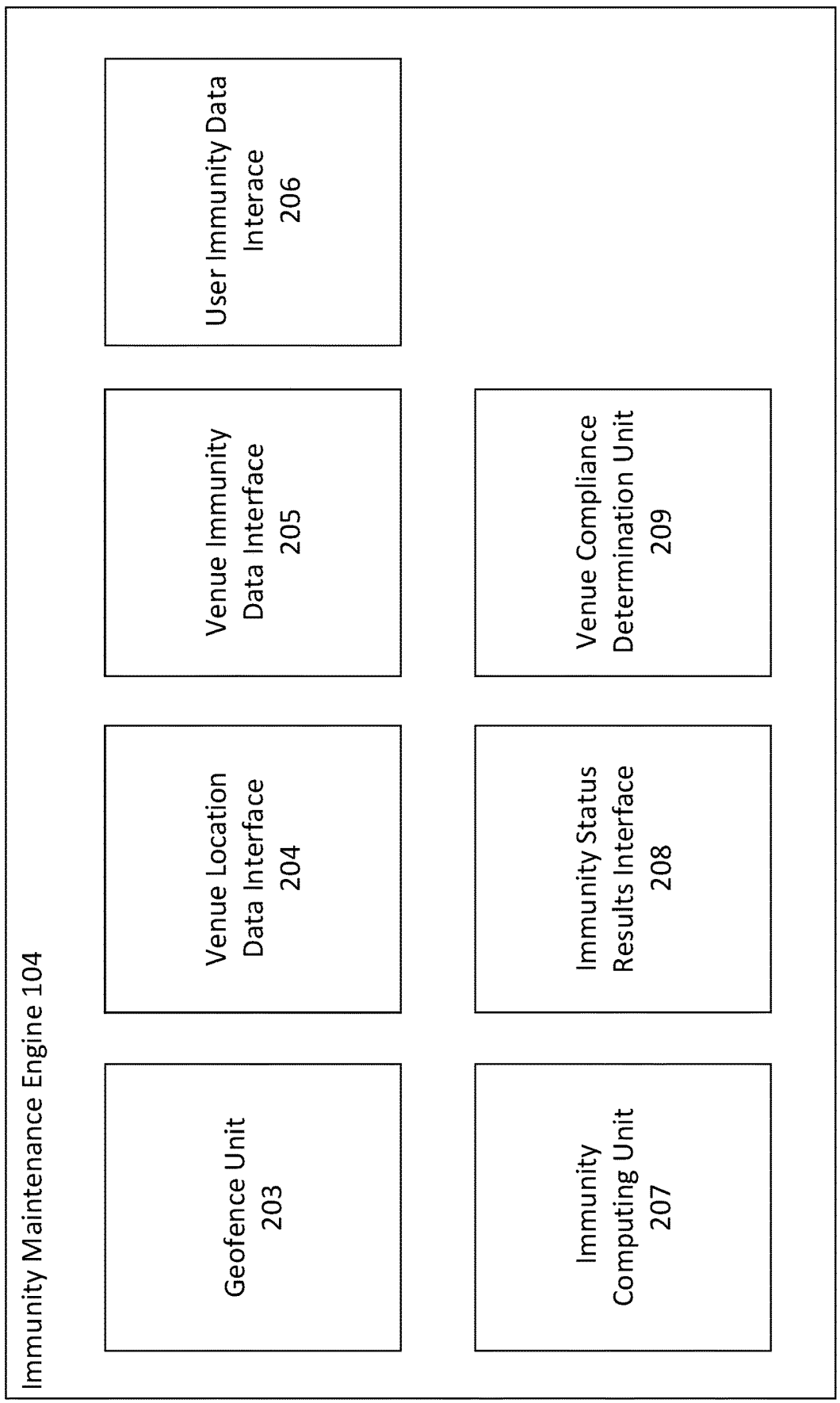
FIG. 2A illustrates a system of the presently disclosed system for immunity monitoring in accordance with an exemplary embodiment of the invention.

FIG. 2A illustrates a system of the presently disclosed system for immunity monitoring in accordance with an exemplary embodiment of the invention. The system may comprise the immunity maintenance engine 104. The immunity maintenance engine 104 may comprise a geofence unit 203, a venue location data interface 204, a venue immunity data interface 205, a user immunity data interface 206, an immunity computing unit 207, an immunity status results interface 208, and/or a venue compliance determination unit 209. Other systems and databases may be used, as would be readily understood by a person of ordinary skill in the art, without departing from the scope of the invention.

The geofence unit 203 may define a search area within which venues are identified. The search area may comprise a parameter of a predetermined range from a user device 101 or from a location specified (e.g., selected, entered, etc.) by a user. The predetermined range may comprise a default setting or a user may specify a range, such as 1 mile, 2 miles, 5 miles, etc. The search area may be defined by a boundary, such as a city, county, etc. The search area may be based on a location of the user device 101. The search area may be based on a location specified by the user. In an alternative embodiment, a user may specify a particular venue.

The venue location data interface 204 may receive messages originated by the venue location data unit 105 via a messaging protocol and prepare the messages in a manner suitable for consumption by the immunity maintenance engine 104. The venue location data interface 204 may receive information in a format usable by the immunity maintenance engine 104 and prepare the messages in a suitable messaging protocol to be ultimately consumed by the venue location data unit 105. For example, the venue location data interface 204 may prepare geofence data created by the geofence unit 203 to be encapsulated in a format suitable for transmission across the network 150 and reception at the venue location data unit 105. As another example, in response to transmitting the geofence data, the venue location data interface 204 may receive location data associated with each venue within the geofence and prepare the received location data in a format usable by the rest of the components and/or modules of the immunity maintenance engine 104. The venue location data interface 204 may send and/or receive messages across a network, such as the network 150. The venue location data interface 204 may send and/or receive messages arranged according to any standard, such as, Internet Protocol (IP), Wi-Fi, Bluetooth, etc.

The venue immunity data interface 205 may receive messages originated by the venue target immunity datastore 106 and/or the venue immunity level datastore 107 via a messaging protocol and prepare the messages in a manner suitable for consumption by the immunity maintenance engine 104. The venue immunity data interface 205 may receive information in a format usable by the immunity maintenance engine 104 and prepare the messages in a suitable messaging protocol to be ultimately consumed by the venue target immunity datastore 106 and/or the venue immunity level datastore 107. For example, the venue immunity data interface 205 may prepare queries based on data received from the venue location data unit 105 for the venue target immunity datastore 106 and the venue immunity level datastore 107 to be encapsulated in a format suitable for transmission across the network 150 and reception at the venue target immunity datastore 106 and the venue immunity level datastore 107. As another example, in response to transmitting the queries, the venue immunity data interface 205 may receive target immunity data and immunity level data (e.g., current immunity level data, historic immunity level data, etc.) for each venue within the geofence and prepare the received target immunity data and immunity level data in a format usable by the rest of the components and/or modules of the immunity maintenance engine 104. The venue immunity data interface 205 may send and/or receive messages across a network, such as the network 150. The venue immunity data interface 205 may send and/or receive messages arranged according to any standard, such as, Internet Protocol (IP), Wi-Fi, Bluetooth, etc.

The user immunity data interface 206 may receive messages originated by the user immunity datastore 108 via a messaging protocol and prepare the messages in a manner suitable for consumption by the immunity maintenance engine 104. The user immunity data interface 206 may receive information in a format usable by the immunity maintenance engine 104 and prepare the messages in a suitable messaging protocol to be ultimately consumed by the user immunity datastore 108. For example, the user immunity data interface 206 may prepare a query based on a QR code for the user immunity datastore 108 to be encapsulated in a format suitable for transmission across the network 150 and reception at the user immunity datastore 108. As another example, in response to transmitting the query, the user immunity data interface 206 may receive user immunity data associated with the QR code and prepare the received user immunity data in a format usable by the rest of the components and/or modules of the immunity maintenance engine 104. The user immunity data interface 206 may send and/or receive messages across a network, such as the network 150. The user immunity data interface 206 may send and/or receive messages arranged according to any standard, such as, Internet Protocol (IP), Wi-Fi, Bluetooth, etc.

The immunity computing unit 207 may perform projected immunity level calculations. The immunity computing unit 207 may perform projected immunity level calculations for a future visit. For example, a user may search for various types of business (e.g., restaurants, bars, gyms, etc.) and specify a search area, as described above. The search results in reception of target immunity data and immunity level data (e.g., current immunity level data, historic immunity level data, etc.) for each venue that fits within parameters of the search, as described above. The immunity computing unit 207 may use the received user immunity data and immunity level data to estimate a projected immunity level data for each venue. The immunity computing unit 207 may use the projected immunity level data and the target immunity data to determine a likelihood of entry into each venue if the user were to go to the venue. The immunity computing unit 207 may cause each venue to be tagged as either "likely accessible" or "likely inaccessible" (or varying degrees in between) according to the determined likelihoods at each venue.

The immunity computing unit 207 may perform projected immunity level calculations for a venue in real-time as patrons enter and exit the venue. For example, a venue may scan immunity reference data to retrieve user immunity data, when deciding if a user should be allowed to enter the venue. The immunity computing unit 207 may use the retrieved user immunity data, as well as immunity level data (e.g., current immunity level data, historic immunity level data, etc.) associated with the venue to determine a projected immunity level data if the user is allowed to enter. The immunity computing unit 207 may use the projected immunity level data and target immunity data associated with the venue to determine if the entry of the user into the venue would result in the venue falling below their target immunity level. In one aspect, the projected immunity level is used to determine if a user is allowed to enter the venue. In one aspect, the projected immunity level is used to notify the venue of the effect on the venue immunity level relative to the target immunity level, such as if the venue would fall below the target immunity level. In one aspect, the projected immunity level is used to make recommendations to a venue regarding allowing/denying entry of a given user into the venue. Such determinations may be communicated to the venue device(s) 103 via immunity status results interface 208 discussed in more detail below. In an embodiment, the venue may update the immunity level data associated with the venue as users leave the venue. In an embodiment, the venue may assume a user leaves the venue after a threshold amount of time.

Figure 2B:
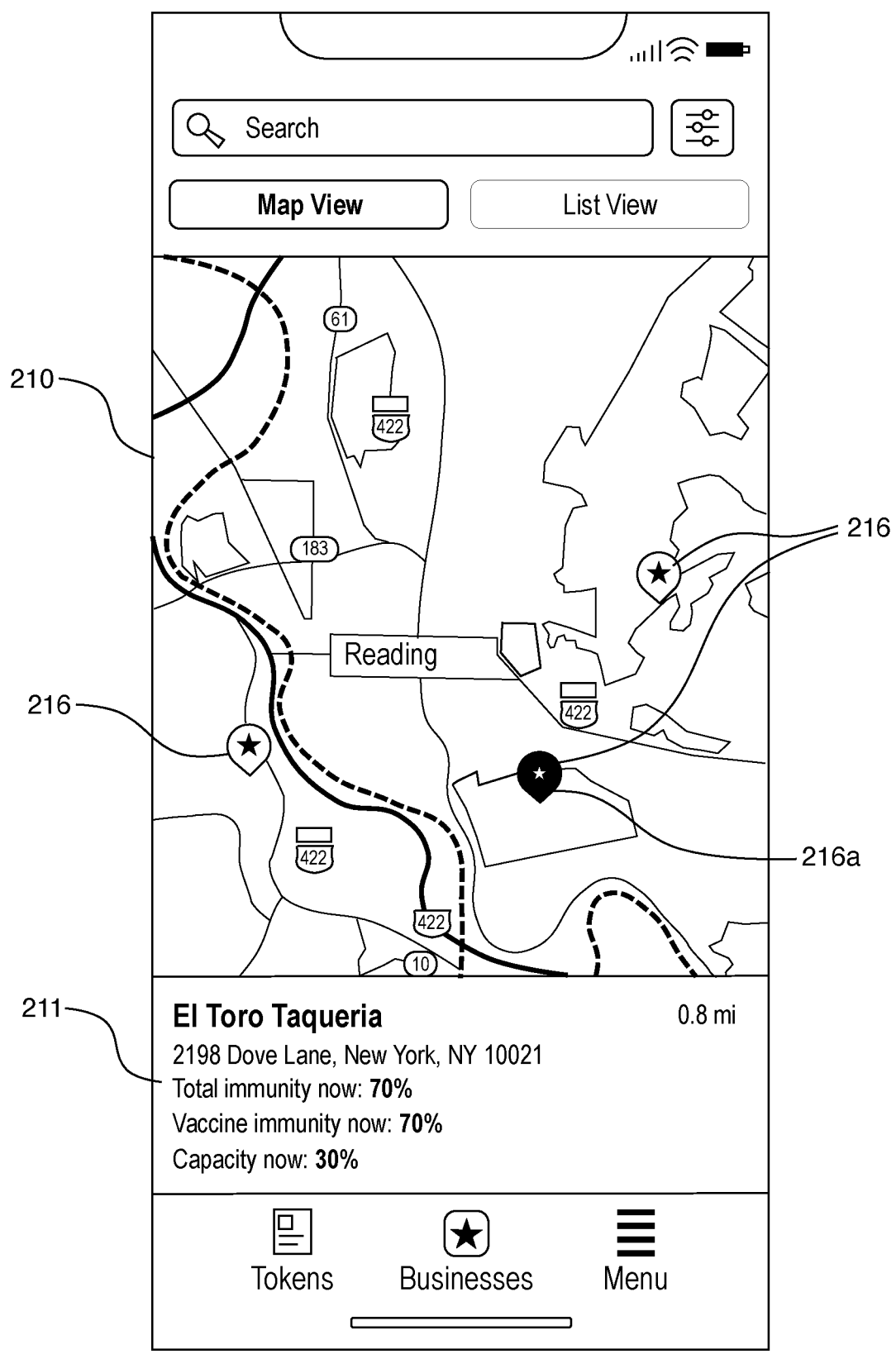
FIG. 2B illustrates a user interface in accordance with an exemplary embodiment of the invention.
Figure 2C:
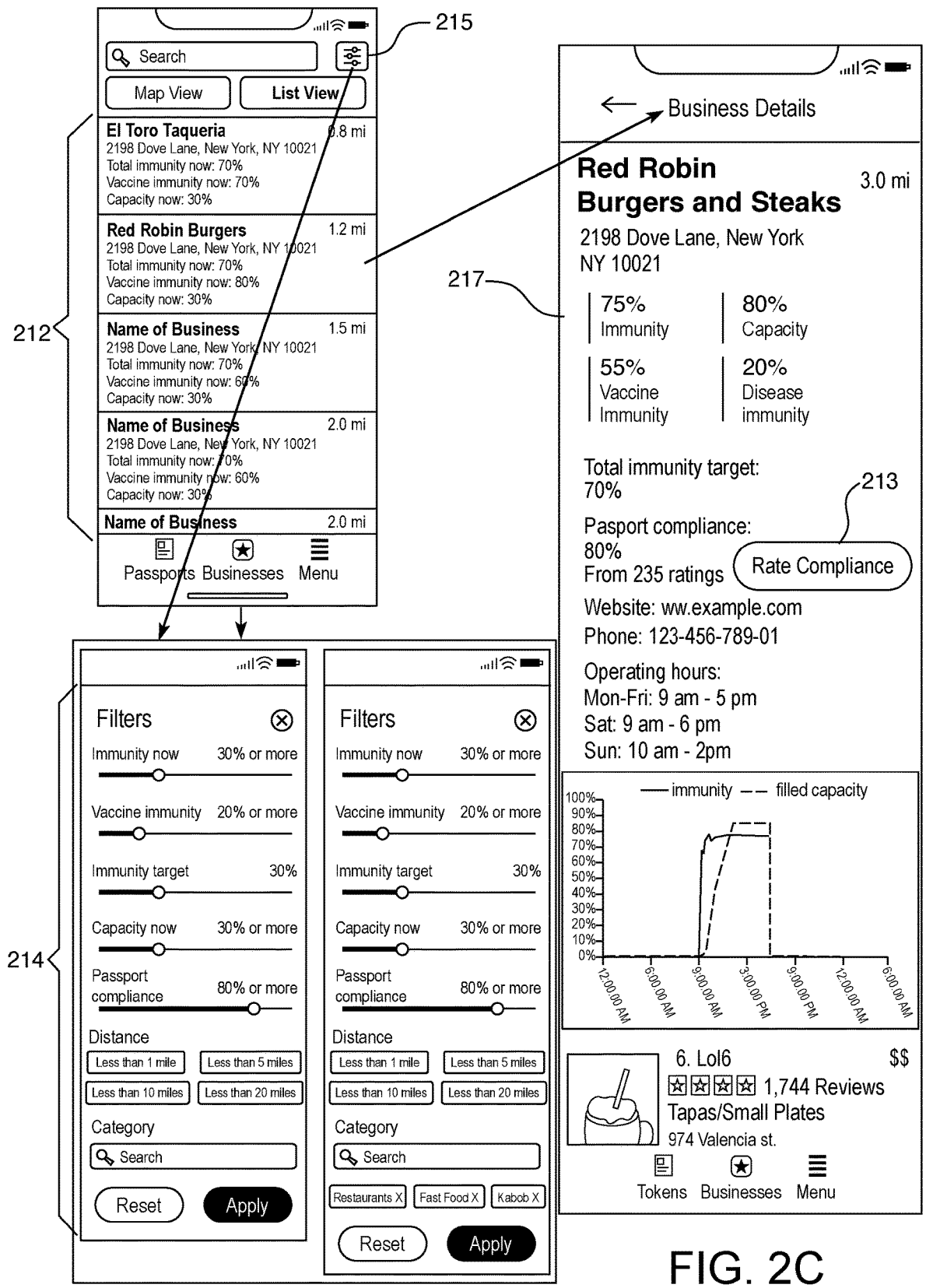
FIG. 2C illustrates a user interface in accordance with an exemplary embodiment of the invention.

The immunity status results interface 208 may receive messages originated by the one or more user device(s) 101 and/or the one or more venue device(s) 103 via a messaging protocol and prepare the messages in a manner suitable for consumption by the immunity maintenance engine 104. The immunity status results interface 208 may receive information in a format usable by the immunity maintenance engine 104 and prepare the messages in a suitable messaging protocol to be ultimately consumed by the one or more user device(s) 101 and/or the one or more venue device(s) 103. For example, the immunity status results interface 208 may provide results from the immunity computing unit 207 to be encapsulated in a format suitable for transmission across the network 150 and reception at the one or more user device(s) 101. In an embodiment, the provided results may comprise a likelihood of accessibility into a venue. In an embodiment, the provided results may only include venues with a likelihood of accessibility. In an embodiment, the provided results may comprise all venues within the geofenced area and each venue may comprise a tag indicating a likelihood of accessibility to the venue. The provided results may include statistics, such as current and historical immunity levels (e.g. for the past hour, day, week, etc.) associated with each venue and/or aggregated current and historical immunity levels statistics for the venues in the geofenced area. The provided results may include venue target immunity level and current immunity level statistics for each venue. The provided results may be filtered by a user selected filter. FIG. 2B and FIG. 2C comprise interfaces for displaying accessibility data associated with venues within a searched geofence.

As another example, the immunity status results interface 208 may provide results from the immunity computing unit 207 to be encapsulated in a format suitable for transmission across the network 150 and reception at the one or more venue device(s) 103. In an embodiment, a venue device 103 may scan a user device 101 to capture immunity reference data to retrieve user immunity data associated with a patron wishing to enter a venue. The venue device 103 may receive an indication of an immunity level if the patron is allowed to enter the venue. The venue device 103 may receive a notification (e.g., alarm, alert, etc.) if admitting a patron will put the venue below an associated target immunity level. In an embodiment, a venue may use the results from the immunity status results interface 208 to influence an entry decision, but ultimately may make an entry and/or denial decision by other factors (e.g., the employee can see that a big party of unvaccinated people is about to leave, the employee can see that a big party of vaccinated people is about to leave, etc.). In an embodiment, a venue may have an automated gate and the result given to the venue device 103 may dictate whether a patron is allowed to enter the venue or not. The immunity status results interface 208 may send and/or receive messages across a network, such as the network 150. The immunity status results interface 208 may send and/or receive messages arranged according to any standard, such as, Internet Protocol (IP), Wi-Fi, Bluetooth, etc.

The venue compliance determination unit 209 may determine (e.g., compute, calculate, etc.) a score associated with each venue. The score may indicate how reliable the venue is at requesting user immunity data. A user that visits a venue may be asked if the user and/or all the members in the user's group were asked to provide user immunity data. The venue compliance determination unit 209 may compile user responses to calculate the percentage of users asked for user immunity data and use the percentage to, in part, determine the score. The score may, in part, indicate how reliable the venue is at maintaining an immunity level at or above its target immunity level. The score may, in part, indicate how reliable the venue is at maintaining an immunity level at or above a particular threshold, such as a level mandated by rule, law, and/or regulation. The score may, in part, indicate how reliable the venue is at maintaining an immunity level at or above a user selected immunity level.

FIG. 2B illustrates a user interface in accordance with an exemplary embodiment of the invention. The user interface shows what may be shown on one of the one or more user device(s) 101. The interface may comprise current and historical aggregated data 211 for a selected venue 216a within a geofenced area (e.g., region, location, etc.). The aggregated data may be presented in a manner indicating approval (e.g., in green, with a check mark, etc.) when the data is at or above a particular target immunity level. The aggregated data may be presented in a manner indicating warning or caution (e.g., in red, with an X, etc.) when the data is below the particular target immunity level. The interface may comprise a visual representation (e.g., map, etc.) of the geofenced area 210. The visual representation may comprise a representation of each venue 216 within the geofenced area.

FIG. 2C illustrates a user interface in accordance with an exemplary embodiment of the invention. The user interface shows what may be shown on one of the one or more user device(s) 101. The interface may comprise at least a portion of the venues in the geofenced area. The interface may comprise fields 212 associated with the venues. The fields 212 may comprise a name, one or more categories, an address, an immunity target level, current immunity level, historic immunity levels, a compliance score, a compliance button (e.g., link, engageable element, etc.), a directions button, a website button, a contact (e.g., call, email, etc.) button, etc. On engagement (e.g. tapping, clicking, etc.) of a venue within fields 212, an individual venue information interface 217 is accessed and presented. The individual venue information interface 217 may comprise venue information including, but not limited to venue name, venue address, venue website, venue operating hours, venue phone number, venue immunity statistics (e.g. current, historical), venue compliance score, etc. In addition, to being presented as part of fields 212, a compliance button 213 may additionally or alternatively, be presented on an individual venue information interface 217. On engagement of (e.g., clicking, pressing, etc.) the compliance button associated with a venue, a compliance interface (e.g., window, pop-up, site, screen, etc.) may be displayed (e.g., launched, popped-up, navigated to, etc.). Compliance interface may allow a user to give compliance feedback, as described above. The set of venues and associated fields 212 displayed may be changed through a filter button and/or a sort button 215. On engagement of the button 215, interface 214 may be displayed. Interface 214 may allow a user to filter venues by target immunity level, historical immunity level, actual immunity level, compliance score, distance, categories (e.g., cuisine served, venue type, etc.), etc. Interface 214 may allow a user to sort venues by target immunity level, historical immunity level (e.g., last hour, today, yesterday, last 7 days, last 30 days, etc.), actual immunity level (e.g., current, real-time), compliance score, distance, categories (e.g., cuisine served, venue type, etc.), etc.

Figure 3A:
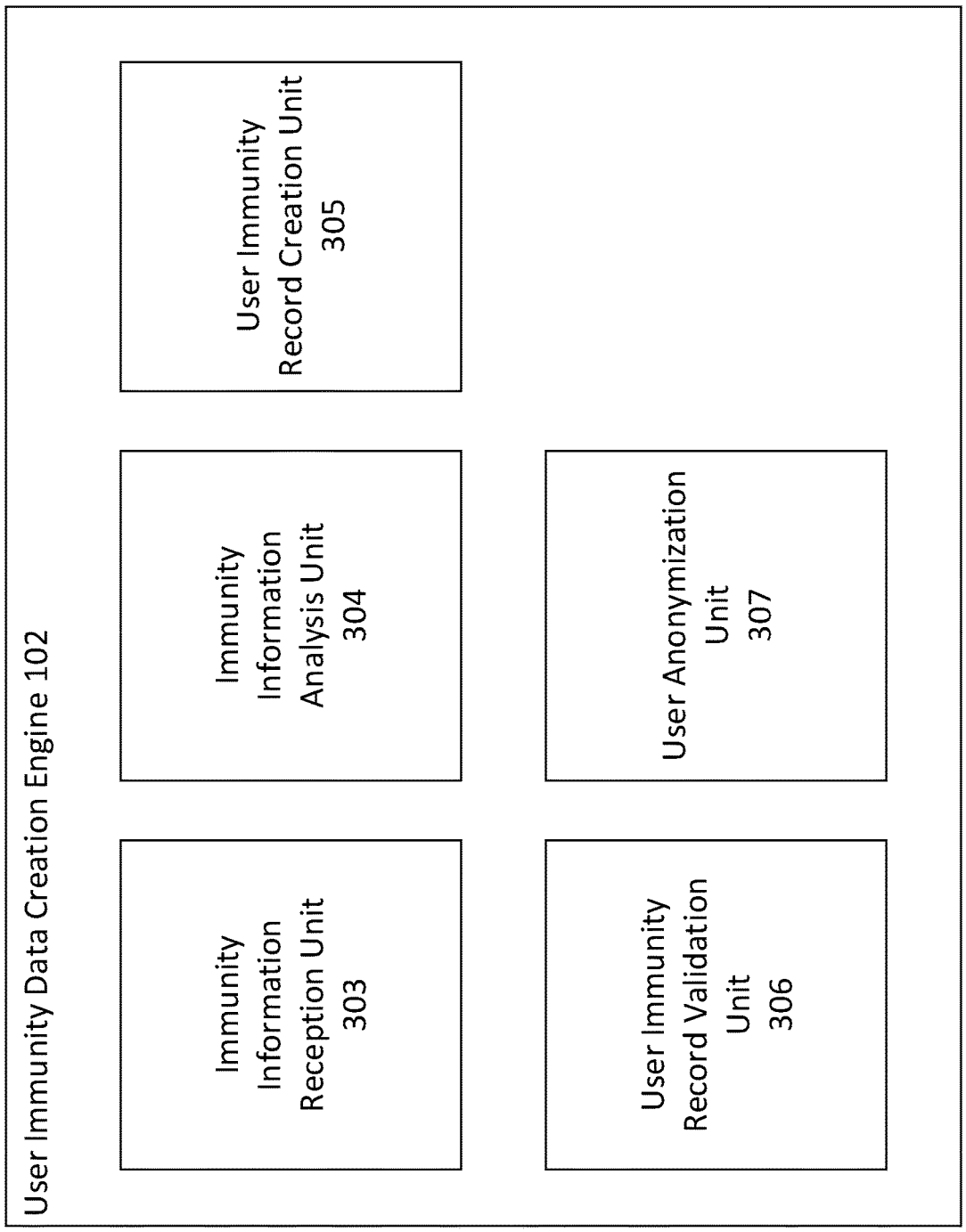
FIG. 3A illustrates a system of the presently disclosed system for immunity data creation in accordance with an exemplary embodiment of the invention.

FIG. 3A illustrates a system of the presently disclosed system for immunity data creation in accordance with an exemplary embodiment of the invention. The system may comprise the user immunity data creation engine 102. The user immunity data creation engine 102 may comprise an immunity information reception unit 303, an immunity information analysis unit 304, a user immunity record creation unit 305, a user immunity record validation unit 306, and/or a user anonymization unit 307. Other systems and databases may be used, as would be readily understood by a person of ordinary skill in the art, without departing from the scope of the invention.

Figure 3B:
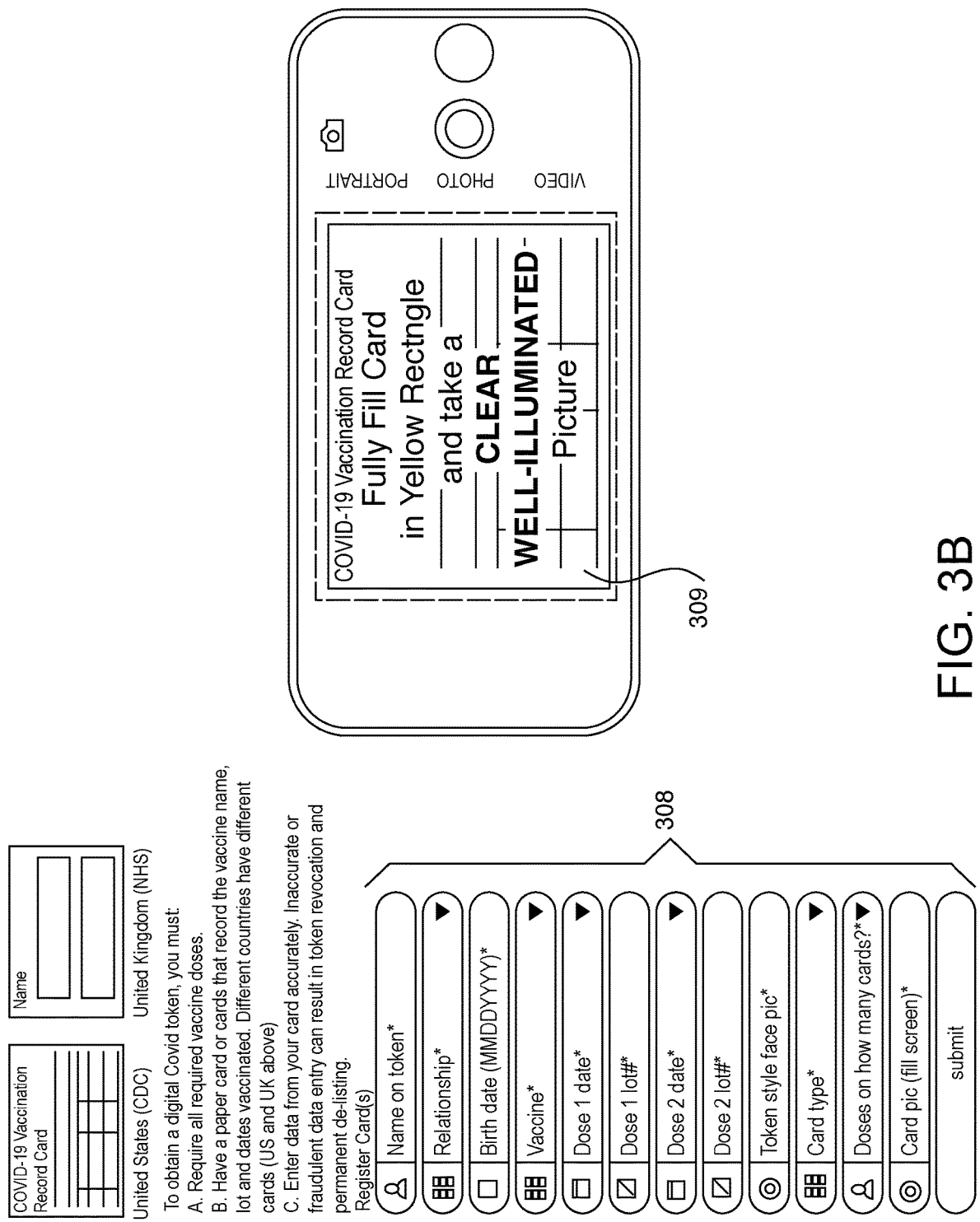
FIG. 3B illustrates a user interface in accordance with an exemplary embodiment of the invention.

The immunity information reception unit 303 may receive immunity information from a user device 101. The immunity information reception unit 303 may receive information manually entered by a user. The immunity information reception unit 303 may receive selections from drop down menus. FIG. 3B (left) shows an example user interface for receiving selections from drop down menus or via text data entry 308. The immunity information reception unit 303 may receive a digital image of a medical record, such as an image of an identification card, antibody or prior infection test results, or a vaccination card or passport. FIG. 3B (right) shows an example user interface 309 for receiving a digital image.

The immunity information analysis unit 304 may process information received by the immunity information reception unit 303. The immunity information analysis unit 304 may perform OCR on a digital image received by the immunity information reception unit 303. The immunity information analysis unit 304 may extract data from the OCR'ed digital image.

The user immunity record creation unit 305 may use the data received from the immunity information reception unit 303 and/or extracted by the immunity information analysis unit 304 to create user immunity data for storage in the user immunity datastore 108. The user immunity record creation unit 305 may create immunity reference data associated with the user immunity data. The immunity reference data may comprise a unique identifier, such as a barcode or QR code, which, when engaged, retrieves corresponding user immunity data from the user immunity datastore 108. The immunity reference data may be provided to a corresponding user device 101 or venue device 103 for retrieval of the corresponding user immunity data from the user immunity datastore 108.

Figure 3C:
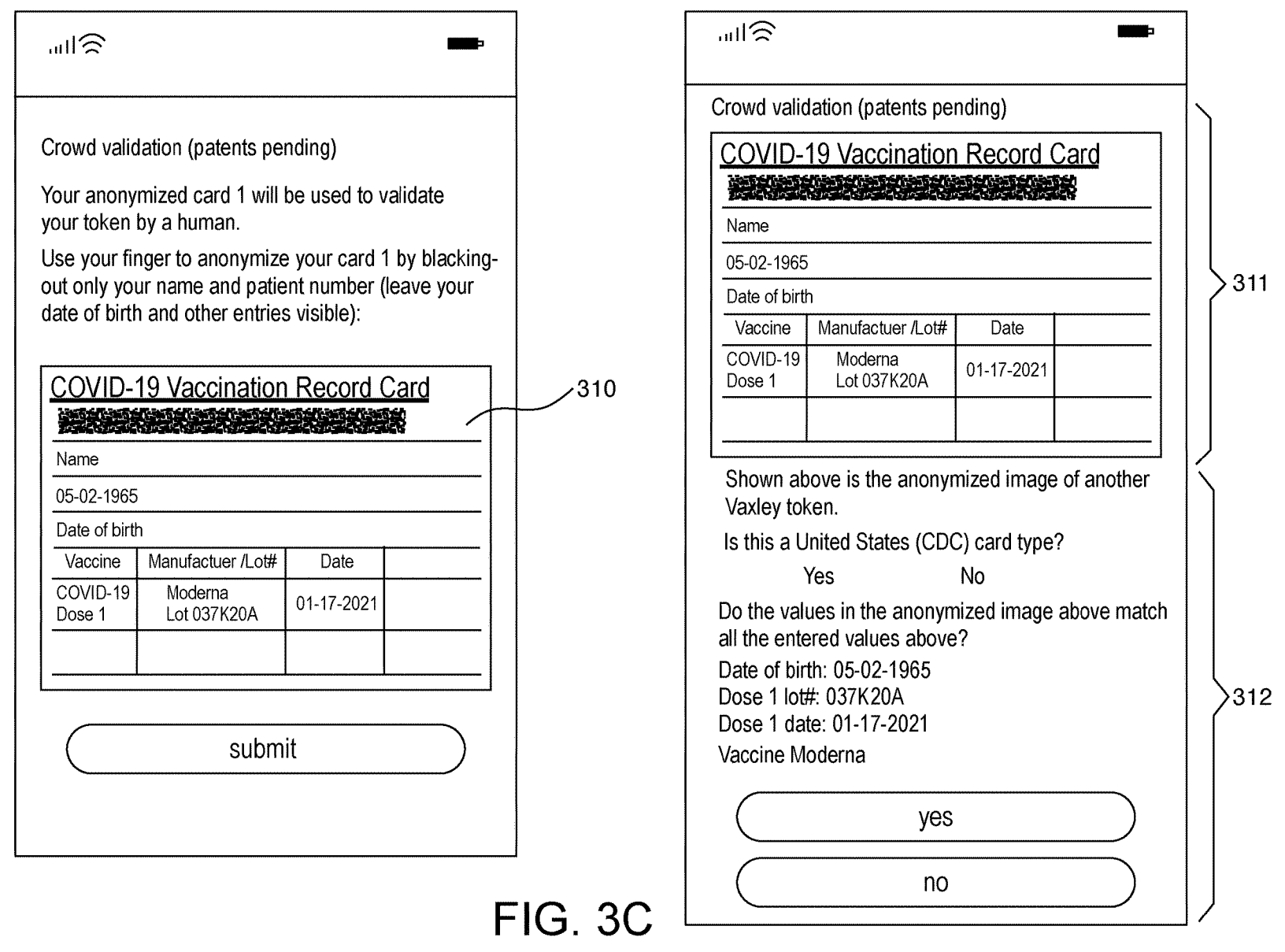

The user anonymization unit 307 may receive redaction data to conceal sensitive information from the received digital image of the medical record. In an embodiment, a user may swipe over sensitive information on the digital image, causing an object to obstruct an area of the digital image corresponding to the swipe. Redaction data may comprise information corresponding to the area swiped. In one embodiment a user is instructed which letters in a field to swipe to create a pseudonym or pseudo-data representation of the sensitive information. For example, a user may be instructed to swipe over every other letter in their concatenated first and last names to create a single anonymized pseudonym for the name. Other letter selections are possible (e.g. every second, random, etc.). When reproduction of an anonymized version of the digital image is needed, the redaction data may be used to determine areas of the reproduced digital image to conceal. FIG. 3C (left) shows an example user interface for receiving redaction information. The user anonymization unit 307 may automatically obstruct portions of fields, such as, for example, by automatically redacting certain letters in a name. Redaction information may comprise the certain redacted letters in corresponding fields.

The user immunity record validation unit 306 may provide data to user devices 101 to validate the data (crowd validation). The user immunity record validation unit 306 may provide a digital image received by the immunity information reception unit 303 as modified by the redaction information received by the user anonymization unit 307 to the user devices 101. The user immunity record validation unit 306 may provide immunization fields to the user devices 101. The user immunity record validation unit 306 may cause a prompt for confirmation to be displayed to the user devices 101, wherein confirmation indicates that the immunization fields match the information in the redacted digital image. FIG. 3C (right) shows an example user interface for verifying immunity information. When a threshold percentage and/or a threshold number of user devices 101 verify (e.g., confirm, validate, etc.) that the immunization fields match the information in the redacted digital image, the corresponding immunization information may be considered verified. In an embodiment, a validation status may comprise "validated", "pending validation", "unvaccinated", etc.

FIG. 3B illustrates a user interface in accordance with an exemplary embodiment of the invention. The user interface shows what may be shown on one of the one or more user device(s) 101. The user interface may be used to capture user immunity information. The interface may comprise instructions. The interface may comprise a plurality of fields 308. The plurality of fields 308 may comprise fields for capturing a name, relationship to user, birth date, vaccine brand (e.g., manufacturer, etc.), first dose date, first dose lot number, second dose date, second dose lot number, a picture of the user, a card type, a number of cards, a card picture, indication of completion, etc such as via manual data entry or via selection of items from lists. Additionally or alternatively, the user interface may be used to capture a digital image of a card, such as a vaccination card. The interface may comprise an area 309 within which a medical record, such as a vaccination card or test report, should be in the screen when a digital image of the medical record is captured.

FIG. 3C illustrates a user interface in accordance with an exemplary embodiment of the invention. The user interface shows what may be shown on one of the one or more user device(s) 101. The user interface may be used to capture redaction information 310. The user interface may display a card. A user may swipe on the user interface to produce an obstruction of sensitive information. The obstruction produced by the swipe may represent redaction information 310.

FIG. 3C illustrates a user interface in accordance with an exemplary embodiment of the invention. The user interface shows what may be shown on one of the one or more user device(s) 101. The user interface may be used to verify immunity information (e.g., by crowd validation). The user interface may comprise a redacted version of a vaccination card 311. The user interface may comprise a feedback section 312. The feedback section 312 may comprise immunity information, an accept button, a reject button, etc. The immunity information may comprise a vaccine distributing body (e.g., a country, a state, an athletic body, etc.), a birth date, a vaccine brand (e.g., manufacturer, etc.), a first dose date, a first dose lot number, a second dose date, a second dose lot number, etc.

Figure 4:
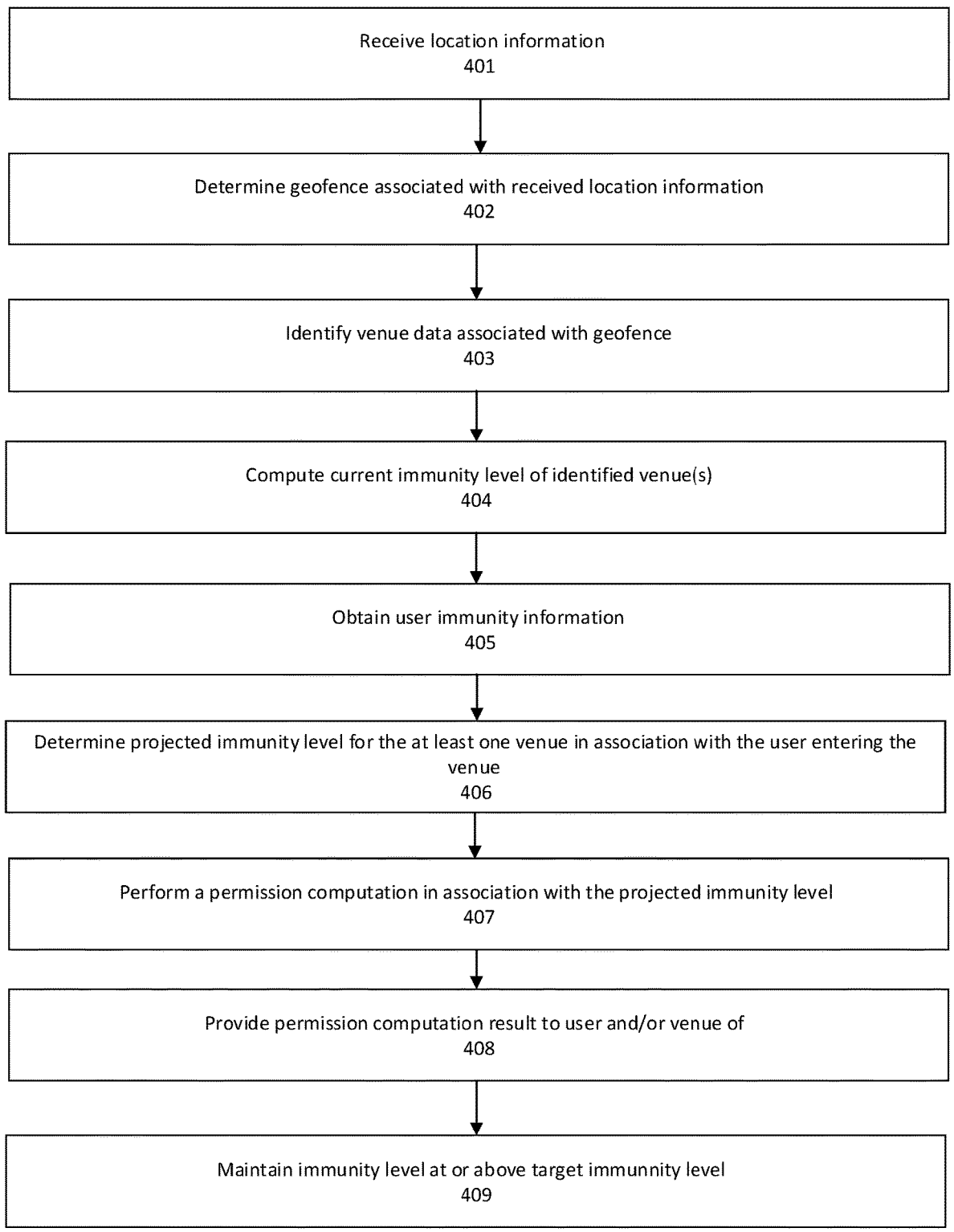
FIG. 4 illustrates a flowchart for immunity monitoring in accordance with an exemplary embodiment of the invention.

FIG. 4 illustrates, in an example embodiment, method 400 of immunity monitoring (e.g., management, maintenance, etc.). In embodiments, the method steps or techniques depicted and described herein can be performed in a processor of the immunity maintenance engine 104, the method steps being encoded as processor-executable instructions in a non-transitory memory of the immunity maintenance engine 104. In embodiments, the method steps or techniques depicted and described herein can be performed in a processor of the one or more user device(s) 101, the method steps being encoded as processor-executable instructions in a non-transitory memory of the one or more user device(s) 101. In embodiments, the method steps or techniques depicted and described herein can be performed in a processor of the one or more venue device(s) 103, the method steps being encoded as processor-executable instructions in a non-transitory memory of the one or more venue device(s) 103. The techniques of FIG. 4 may be implemented in an operating system kernel, in a separate user process, in a library package bound into network applications, on a specially constructed machine, on an application-specific integrated circuit (ASIC), or a field programmable gate array (FPGA). The order of steps depicted in FIG. 4 is merely exemplary and the steps may be arranged in varying orders and/or be performed concurrently as would be understood by a person of ordinary skill in the art without departing from the scope of the inventive concepts.

At step 401, location data (e.g., information, etc.) may be received. The location data may be received from a computing device associated with the user, such as one of the user device(s) 101 in FIG. 1. The received location data may comprise current location data obtained from a computing device associated with the user. The received location data may be computed based on a location chosen by a user on a graphical user interface of a computing device associated with the user.

At step 402, a geofence associated with the received location data may be computed (e.g., determined, etc.). The geofence may be computed based on contextual information associated with the received location data. The contextual information may comprise data indicating a distance a user has moved within a threshold period of time. A determination may be made of movement speed of the user by dividing the distance moved by the duration of the threshold period of time.

At step 403, venue data associated with at least one venue associated with the computed geofence may be identified. Each venue may be associated with a target immunity level. The immunity target level may be equal to or greater than the herd immunity threshold of a virus. The virus may be selected from the group consisting of SARS-CoV-1, SARS-CoV-2 and variants thereof.

At step 404, a current immunity level associated with each venue may be computed (e.g., calculated, etc.). The current immunity level may be computed based on immunity data associated with each venue occupant who has provided immunity data in association with entering, and optionally also exiting, the corresponding venue. At least one venue may comprise an infection of the occupants by the virus. The infection may have a growth rate. The growth rate may comprise a negative value. Over time the infection may optionally disappear. A plurality of venues may contain occupants that total more than 10,000, 100,000, 1,000,000, 10,000,000 or more than 100,000,000 people. The current immunity level may be calculated (e.g., computed, etc.) by dividing the sum of occupants in the venue with (a) vaccine immunity and (b) disease immunity by the sum of occupants in the venue with (a) vaccine immunity, (b) disease immunity and (c) no immunity.

At step 405, immunity data associated with the user may be obtained. The immunity data may be obtained from a database. The database may be at least partially populated from data provided by the user. The immunity data may comprise a designation of (a) vaccine immunity, (b) disease immunity, or (c) no immunity. The immunity data may comprise at least one of image data, text data, and validation data. The image data may comprise an image of a user associated with the immunity data. The text data may comprise at least one of user name, user date of birth, manufacturer of vaccination received, vaccination date, number of vaccination doses received and associated dates, test result, manufacturer of test conducted, date of test result, and an expiration date associated with the immunity data. The validation data may comprise an indication that the immunity data is at least one of confirmed, pending confirmation, or invalid. The validation data may be determined based on input received from a threshold number of other users on a threshold number of entries that are presented for validation purposes. The validation data may be determined by presenting at least one image of a medical record that is partially redacted to other users and receiving input from at least one other user regarding the validity of information present in the partially redacted image of the medical record. The input received from at least one other user may be provided on a computing device associated with the at least one other user. Obtaining the immunity data may comprise receiving an image of a machine readable optical identifier associated with the user (e.g., barcode, QR code). The machine readable optical identifier may be used to acquire immunity information associated with the user from the database. The immunity data may be created in association with at least one of receiving an image of a medical record and performing optical character recognition on the image of the medical record, and receiving user entered information. The redaction may comprise redacting alternating letters in the name of the user to encrypt and conceal the identity of the user while still identifying the user with a unique pseudonym.

At step 406, a determination may be made of whether the user is enabled to access each venue based on a permissions computation comprising a projected immunity level for each venue. The projected immunity level may be calculated based on data associated with the computed current immunity level and immunity data of the user, and comparing the projected immunity level if the user were to access each venue with the target immunity level associated with the venue. The projected immunity level may be calculated the same as the current immunity level assuming the user were to enter the venue and become an occupant by combining data associated with the current immunity level and immunity data associated with the user.

At step 407, venue data associated with each venue that the user is enabled to access may be provided to the computing device associated with the user based on the permissions computation, the provided venue data, target immunity level, and current immunity level capable of being displayed on the computing device associated with the user. The venue data may be obtained from a database that stores venue names and venue locations, optionally via an application programming interface.

At step 408, access may be granted or denied to the user to each venue based on the permissions computation.

At step 409, an immunity level may be maintained at each venue that equals or exceeds the target immunity level associated with each venue. The immunity level may be maintained at more than 100 venues. The immunity level may be maintained at more than 10,000 venues. The immunity level may be maintained at more than 100,000 venues. The immunity level may be maintained at more than 1,000,000 venues. In a preferred embodiment, the immunity level maintained is at or above the herd immunity threshold for a virus (e.g. SARS-CoV-1 or SARS-CoV-2 and variants thereof).

Optionally, compliance data associated with each venue may be computed. The compliance data may provide an indication associated with how often each venue requests immunity data from users. The compliance data may be determined based on input received from users. The compliance data may comprise a calculation associated with a number of users who have entered the venue who were asked to provide immunity data divided by the sum of the number of users who entered the venue that were asked to provide immunity data and the number of users who entered the venue that were not asked to provide immunity data.

Figure 5:
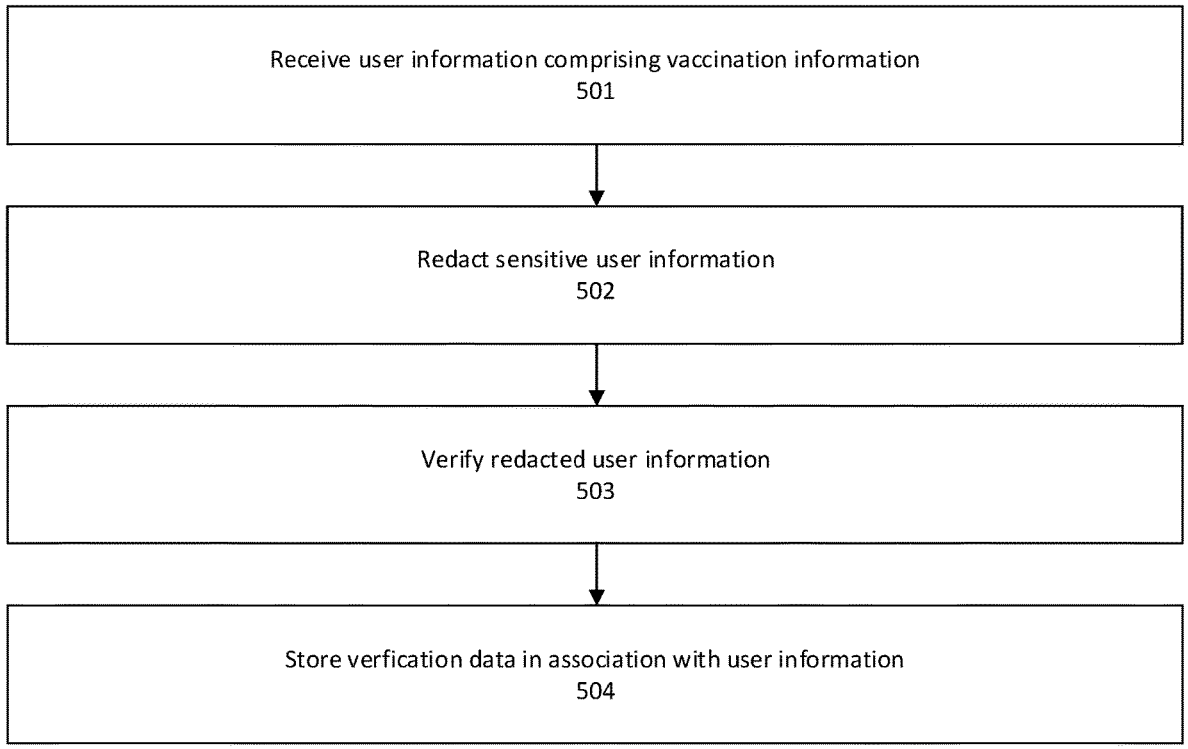
FIG. 5 illustrates a flowchart for immunity data creation in accordance with an exemplary embodiment of the invention.

FIG. 5 illustrates, in an example embodiment, method 500 of immunity data creation. In embodiments, the method steps or techniques depicted and described herein can be performed in a processor of the user immunity data creation engine 102, the method steps being encoded as processor-executable instructions in a non-transitory memory of the user immunity data creation engine 102. In embodiments, the method steps or techniques depicted and described herein can be performed in a processor of the one or more user device(s) 101, the method steps being encoded as processor-executable instructions in a non-transitory memory of the one or more user device(s) 101. In embodiments, the method steps or techniques depicted and described herein can be performed in a processor of the one or more venue device(s) 103, the method steps being encoded as processor-executable instructions in a non-transitory memory of the one or more venue device(s) 103. The techniques of FIG. 5 may be implemented in an operating system kernel, in a separate user process, in a library package bound into network applications, on a specially constructed machine, on an application-specific integrated circuit (ASIC), or a field programmable gate array (FPGA).

At step 501, user information comprising vaccination information may be received. Vaccination information may comprise one or more of the following: a vaccine brand (e.g., manufacturer, creator, sponsor, etc.), a dosage, a dose lot number, a vaccination date, a location, a physician name, an expiration date, a country, a card type, etc. User information may comprise a user name, a date of birth, a validation status, etc. Vaccination information may comprise a digital image representative of a vaccination card or antibody or prior infection test result. Vaccination information may comprise text entered into one or more input fields.

At step 502, redaction information may be received. The redaction information may correspond to a swipe on a screen of a user device. Redaction information may be represented by a black box. The black box may correspond to a location swiped on a screen of a user device. The black box may conceal sensitive user information.

At step 503, redacted user information may be verified. Redacted user information may comprise received user information and/or received redacted information. The redacted user information may be presented to a plurality of other users for verification (crowd validation). Presenting redacted user information to a plurality of other users for verification may comprise presenting the user information to user devices associated with the plurality of other users, wherein the redaction information may be used to conceal sensitive information. Feedback regarding the veracity of the presented redacted user information may be received from the plurality of other users. The redacted user information may be considered verified if a threshold percentage of the plurality of other users confirm the veracity of the redacted user information.

At step 504, verification data may be stored in association with the user information. A barcode or QR code may be created which, when scanned, confirms and/or provides the verified unredacted and/or redacted user information.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the embodiments disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific embodiments, at least some of the features or functionalities of the various embodiments disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some embodiments, at least some of the features or functionalities of the various embodiments disclosed herein may be implemented in one or more virtualized computing environments (e.g., network computing clouds, virtual machines hosted on one or more physical computing machines, or other appropriate virtual environments).

Figure 6:
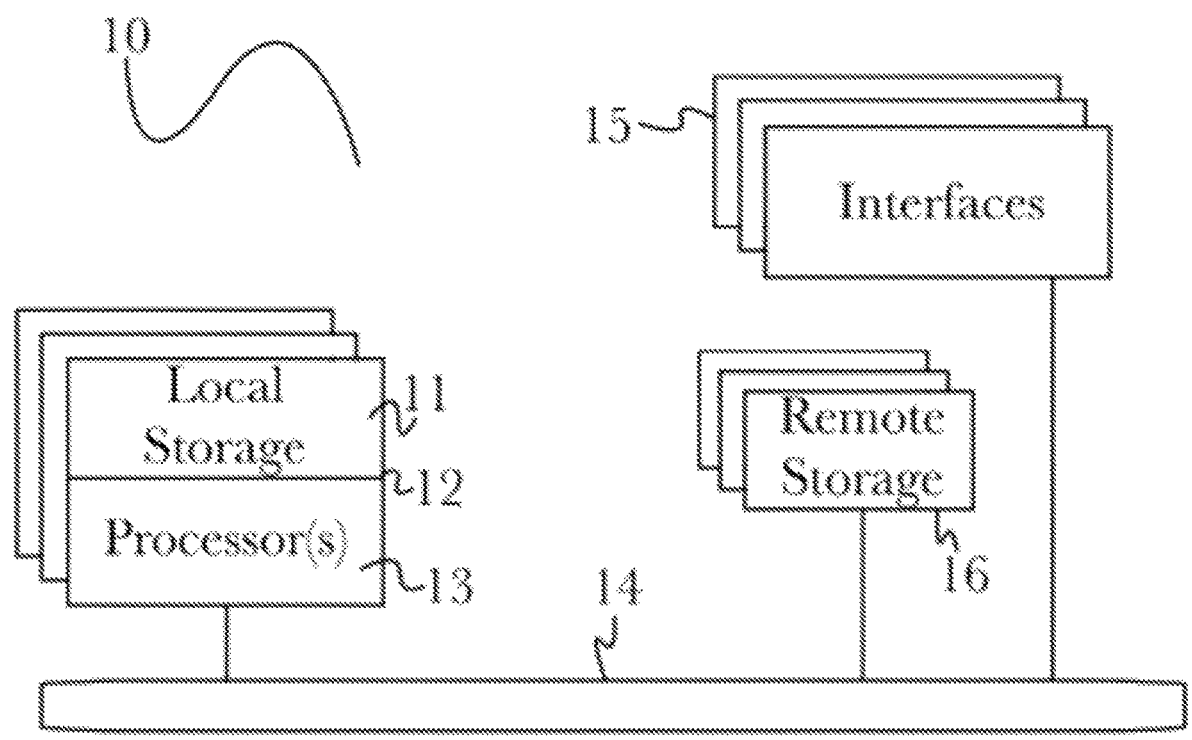
FIG. 6 illustrates components of an exemplary computing device that supports an embodiment of the inventive disclosure.

Referring now to FIG. 6, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some embodiments, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random-access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 6 illustrates one specific architecture for a computing device 10 for implementing one or more of the embodiments described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, single processor 13 handles communications as well as routing computations, while in other embodiments a separate dedicated communications processor may be provided. In various embodiments, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the embodiments described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

The user device(s) 101, the user immunity data creation engine 102, the venue device(s) 103, the immunity maintenance engine 104, and/or the venue location data unit 105 in FIG. 1 may be and/or comprise the computing device 10.

Because such information and program instructions may be employed to implement one or more systems or methods described herein, at least some network device embodiments may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language such as Swift, Objective C, Java, Kotlin, React Native, Appcelerator, Flutter, Dart, Cordova/PhoneGap, etc.).

Figure 7:
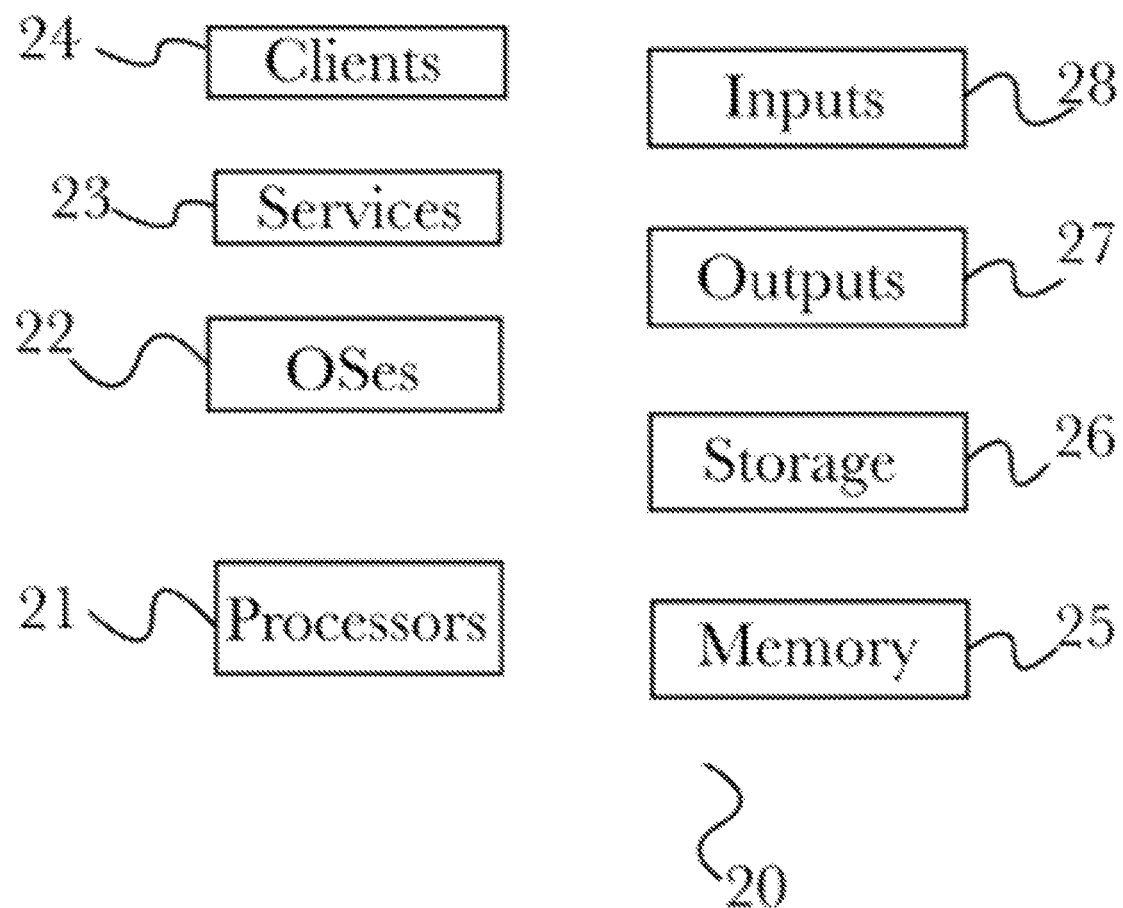
FIG. 7 illustrates one embodiment of a standalone computing system that supports an embodiment of the inventive disclosure.

In some embodiments, systems may be implemented on a standalone computing system. Referring now to FIG. 7, there is shown a block diagram depicting a typical exemplary architecture of one or more embodiments or components thereof on a standalone computing system. Computing device 20 includes processors 21 that may run software that carry out one or more functions or applications of embodiments, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 6). Examples of storage devices 26 include flash memory, magnetic hard drive, CD-ROM, and/or the like.

The user device(s) 101, the user immunity data creation engine 102, the venue device(s) 103, the immunity maintenance engine 104, and/or the venue location data unit 105 in FIG. 1 may be and/or comprise the system 20.

Figure 8:
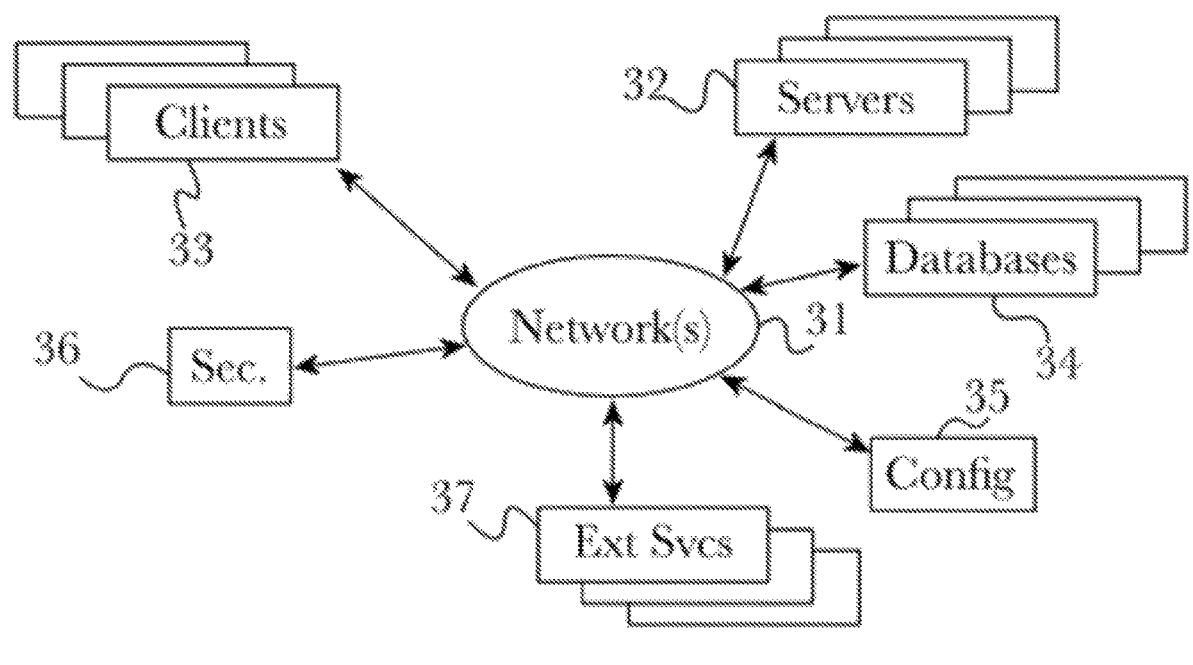
FIG. 8 illustrates an exemplary distributed computing network that supports an exemplary embodiment of the inventive disclosure.

In some embodiments, systems may be implemented on a distributed computing network, such as one having any number of clients and/or servers. Referring now to FIG. 8, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 7. In addition, any number of servers 32 may be provided for handling requests received from one or more clients 33. Clients 33 and servers 32 may communicate with one another via one or more electronic networks 31, which may be in various embodiments any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some embodiments, servers 32 may call external services 37 when needed to obtain additional information, or to refer to additional data concerning a particular call. Communications with external services 37 may take place, for example, via one or more networks 31. In various embodiments, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises.

In some embodiments, clients 33 or servers 32 (or both) may make use of one or more specialized services or appliances that may be deployed locally or remotely across one or more networks 31. For example, one or more databases 34 may be used or referred to by one or more embodiments. It should be understood by one having ordinary skill in the art that databases 34 may be arranged in a wide variety of architectures and using a wide variety of data access and manipulation means. For example, in various embodiments one or more databases 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some embodiments, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some embodiments may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with embodiments without limitation, unless a specific security 36 or configuration system 35 or approach is specifically required by the description of any specific aspect.

The user device(s) 101, the user immunity data creation engine 102, the venue device(s) 103, the immunity maintenance engine 104, and/or the venue location data unit 105 in FIG. 1 may be and/or comprise the architecture 30.

Figure 9:
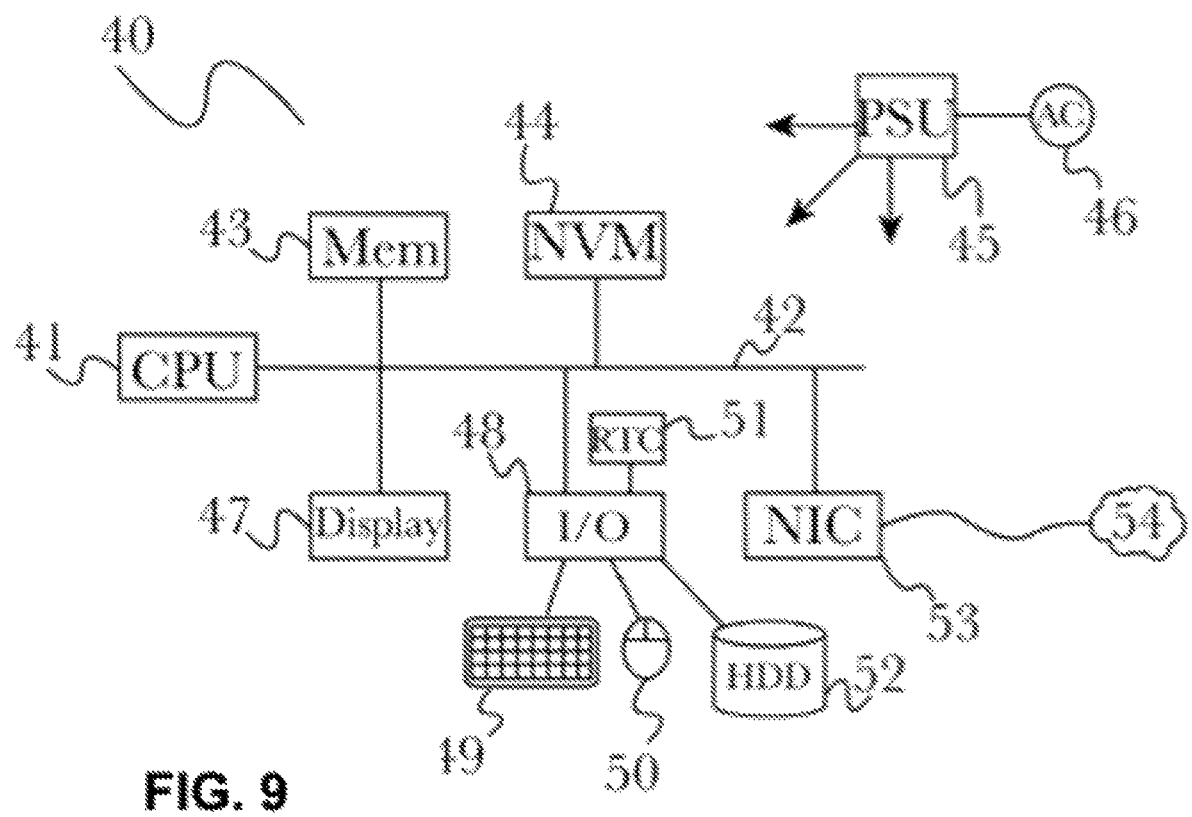
FIG. 9 illustrates an exemplary overview of a computer system that supports an exemplary embodiment of the inventive disclosure.

FIG. 9 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to keyboard 49, pointing device 50, hard disk 52, and real-time clock 51. NIC 53 connects to network 54, which may be the Internet or a local network, which local network may or may not have connections to the Internet. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

The user device(s) 101, the user immunity data creation engine 102, the venue device(s) 103, the immunity maintenance engine 104, and/or the venue location data unit 105 in FIG. 1 may be and/or comprise the computer system 40.

In various embodiments, functionality for implementing systems or methods of various embodiments may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various embodiments described above. Accordingly, the present invention is defined by the claims and their equivalents.

Additional Considerations

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for creating an interactive message through the disclosed principles herein. Thus, while particular embodiments and applications have been illustrated and described, it is to be understood that the disclosed embodiments are not limited to the precise construction and components disclosed herein. Various apparent modifications, changes and variations may be made in the arrangement, operation and details of the method and apparatus disclosed herein without departing from the spirit and scope defined in the appended claims.

What is claimed is:

1. A computer implemented method for message distribution at a venue, the computer implemented method comprising:
   receiving an electronic signal from a computing device associated with a user, wherein the electronic signal is associated with Global Positioning System (GPS) data associated with the computing device;
   automatically computing a geofence based on the received GPS data wherein the computed geofence is comprised of a plurality of venues;
   identifying venue data associated with the plurality of venues associated with the computed geofence, wherein venue data associated with each venue is associated with a target immunity level, the target immunity level representative of a target ratio of occupants within the venue having immunity with respect to total occupants within the venue, the target immunity level being greater than 0% and less than 100%;
   obtaining entry request data associated with the user, wherein the entry request data comprises at least one of a designation of immunity, and a designation of no immunity;

computing a current immunity level associated with each venue, the current immunity level computed based on status data associated with a plurality of venue occupants associated with each venue, the status data associated with the plurality of venue occupants having at least one of a designation of immunity and a designation of no immunity, and wherein the current immunity level is expressed as a ratio of occupants within the venue having immunity with respect to total occupants within the venue, wherein the current immunity level is computed based on entry status data provided by the plurality of occupants in association with at least one of entering and exiting the corresponding venue;

computing a projected immunity level for each venue within the computed geofence, wherein the projected immunity level is calculated based on data associated with the computed current immunity level and the entry request data;

determining whether the user is enabled to access each venue within the plurality of venues within the computed geofence by comparing the projected immunity level with the target immunity level associated with the venue, wherein the comparison indicates that access of the venue by the user would not result in the projected immunity level of the venue falling below the target immunity level associated with the venue; and providing, for display on the computing device associated with the user, results comprising venues that the user would be enabled to access based on the determining whether the user is enabled to access each venue within the plurality of venues within the computed geofence.

2. The computer implemented method of claim 1, wherein the target immunity level is equal to or greater than a herd immunity threshold of a virus.

3. The computer implemented method of claim 2, wherein the virus is associated with an infection having a growth rate, wherein the growth rate is a negative value, and wherein the infection subsides over time.

4. The computer implemented method of claim 3, wherein the virus comprises at least one of SARS-CoV-1, SARS-CoV-2, and variants thereof.

5. The computer implemented method of claim 1, further comprising granting or denying the user access to each venue based on the determining whether the user is enabled to access each venue within the plurality of venues within the computed geofence, thereby maintaining an immunity level at each venue that equals or exceeds the target immunity level associated with each venue, wherein the immunity level is maintained at more than 100 venues, more than 10,000 venues, more than 100,000 venues, or more than 1,000,000 venues.

6. The computer implemented method of claim 1, the venue data associated with the plurality of venues collectively containing occupants that total more than 10,000, 100,000, 1,000,000, 10,000,000 or 100,000,000 people.

7. The computer implemented method of claim 1, wherein the received GPS data comprises at least one of (a) current data obtained from a computing device associated with the user and (b) location data computed based on a location chosen by a user on a graphical user interface of a computing device associated with the user.

8. The computer implemented method of claim 1, wherein the geofence is computed based on contextual information associated with the received GPS data, wherein the contextual information comprises data indicating a distance a user has moved within a threshold period of time, and further comprising determining a movement speed of the user by dividing the distance moved by the duration of the threshold period of time.

9. The computer implemented method of claim 1, wherein the entry request data comprises image data, the image data comprising an image of a user associated with the entry request data.

10. The computer implemented method of claim 1, wherein the entry request data comprises text data, the text data comprising at least one of user name, user date of birth, manufacturer of vaccination received, vaccination date, number of vaccination doses received and associated dates, test result, manufacturer of test conducted, date of test result, and an expiration date associated with the entry request data.

11. The computer implemented method of claim 1, wherein the entry request data comprises validation data, the validation data comprising an indication that the entry request data is at least one of confirmed, pending confirmation, or invalid, and wherein the validation data is determined based on input received from a threshold number of other users on a threshold number of entries that are presented for validation purposes.

12. The computer implemented method of claim 11, wherein the validation data is determined by presenting at least one image of a medical record that is partially redacted to other users and receiving input from at least one other user regarding the validity of information present in the partially redacted image of the medical record, wherein the input received from at least one other user is provided on a computing device associated with the at least one other user.

13. The computer implemented method of claim 12, further comprising automatically redacting alternating letters in the name of the user to encrypt and conceal the identity of the user while still identifying the user with a unique pseudonym.

14. The computer implemented method of claim 1, wherein obtaining the entry request data comprises receiving an image of a machine readable optical identifier associated with the user, wherein the machine readable optical identifier is used to acquire immunity information associated with the user from a database.

15. The computer implemented method of claim 1, wherein the entry request data is created in association with at least one of receiving an image of a medical record and performing optical character recognition on the image of the medical record, and receiving user entered information.

16. The computer implemented method of claim 1, wherein the venue data is obtained from at least one of a database that stores venue names and venue locations, and an application programming interface.

17. The computer implemented method of claim 1, wherein the current immunity level is calculated by dividing A by B, wherein A is the number of occupants in the venue with immunity and B is the total number of occupants in the venue and wherein the projected immunity level is calculated by dividing A' by B', wherein B' is equal to B+1, A' is equal to A+1 if the entry request data associated with the user comprises a designation of immunity, and A' is equal to A if the entry request data associated with the user comprises a designation of no immunity.

18. The computer implemented method of claim 1, further comprising computing compliance data associated with each venue, wherein the compliance data provides an indication associated with how often each venue requests entry request data from users, wherein the compliance data is determined based on input received from users, and wherein the compliance data comprises a calculation associated with a number of users who have entered the venue who were asked to provide entry request data divided by the sum of the number of users who entered the venue that were asked to provide entry request data and the number of users who entered the venue that were not asked to provide entry request data.

19. A computing system for message distribution at a venue, the computing system comprising:
   at least one computing processor; and
   memory including instructions that, when executed by the at least one computing processor, enable the computing system to:
      receive Global Positioning System (GPS) data from a computing device associated with the user;
      automatically compute a geofence associated with the received GPS data, wherein the computed geofence is comprised of a plurality of venues;
      identify venue data associated with the plurality of venues associated with the computed geofence, wherein each venue is associated with a target immunity level, the target immunity level representative of a target ratio of occupants within the venue having immunity with respect to total occupants within the venue, the target immunity level being greater than 0% and less than 100%;
      obtain entry request data associated with the user, wherein the entry request data comprises at least one of a designation of immunity, and a designation of no immunity;
      compute a current immunity level associated with each venue, the current immunity level computed based on status data associated with a plurality of venue occupants associated with each venue, the status data associated with the plurality of venue occupants having at least one of a designation of immunity and a designation of no immunity, and wherein the current immunity level is expressed as a ratio of occupants within the venue having immunity with respect to total occupants within the venue, wherein the current immunity level is computed based on entry request data provided by the plurality of occupants in association with at least one of entering and exiting the corresponding venue;
      compute a projected immunity level for each venue within the computed geofence, wherein the projected immunity level is calculated based on data associated with the computed current immunity level and the entry request data;
      determine whether the user is enabled to access each venue within the plurality of venues within the computed geofence by comparing the projected immunity level with the target immunity level associated with the venue, wherein the comparison indicates that access of the venue by the user would not result in the projected immunity level of the venue falling below the target immunity level associated with the venue; and
      provide, for display on the computing device associated with the user, results comprising venues that the user would be enabled to access based on the determining whether the user is enabled to access each venue within the plurality of venues within the computed geofence.

20. A non-transitory computer readable storage medium for distributing messages at a venue, the non-transitory computer readable storage medium storing instructions that, when executed by at least one processor of a computing system, causes the computing system to:
   receive Global Positioning System (GPS) data from a computing device associated with the user;
   automatically compute a geofence associated with the received GPS data, wherein the computed geofence is comprised of a plurality of venues;
   identify venue data associated with the plurality of venues associated with the computed geofence, wherein each venue is associated with a target immunity level, the target immunity level representative of a target ratio of occupants within the venue having immunity with respect to total occupants within the venue, the target immunity level being greater than 0% and less than 100%;
   obtain entry request data associated with the user, wherein the entry request data comprises at least one of a designation of immunity, and a designation of no immunity;
   compute a current immunity level associated with each venue, the current immunity level computed based on status data associated with a plurality of venue occupants associated with each venue, the status data associated with the plurality of venue occupants having at least one of a designation of immunity and a designation of no immunity, and wherein the current immunity level is expressed as a ratio of occupants within the venue having immunity with respect to total occupants within the venue, wherein the current immunity level is computed based on entry request data provided by the plurality of occupants in association with at least one of entering and exiting the corresponding venue;
   compute a projected immunity level for each venue within the computed geofence, wherein the projected immunity level is calculated based on data associated with the computed current immunity level and the entry request data;
   determine whether the user is enabled to access each venue within the plurality of venues within the computed geofence by comparing the projected immunity level with the target immunity level associated with the venue, wherein the comparison indicates that access of the venue by the user would not result in the projected immunity level of the venue falling below the target immunity level associated with the venue; and
   provide, for display on the computing device associated with the user, results comprising venues that the user would be enabled to access based on the determining whether the user is enabled to access each venue within the plurality of venues within the computed geofence.

21. The computer implemented method of claim 1, further comprising automatically transmitting at least one message to the computing device associated with the user, the message indicating whether access was granted or denied to the user, and displaying the at least one message on the computing device.

22. The computer implemented method of claim 1, further comprising controlling an automated gate associated with a venue in response to obtaining entry request data and determining whether the user is enabled to access the venue.

* * * * *